United States Patent
Shinoda et al.

(10) Patent No.: US 8,657,121 B2
(45) Date of Patent: Feb. 25, 2014

(54) MICROPARTICLE SORTING APPARATUS, MICROCHIP AND MICROCHIP MODULE

(75) Inventors: Masataka Shinoda, Tokyo (JP); Takeshi Matsui, Tokyo (JP); Akiko Tsuji, Kanagawa (JP); Takeshi Yamasaki, Kanagawa (JP); Shoji Akiyama, Kanagawa (JP)

(73) Assignee: Sony Corporation, Tokyo (JP)

( * ) Notice: Subject to any disclaimer, the term of this patent is extended or adjusted under 35 U.S.C. 154(b) by 257 days.

(21) Appl. No.: 13/096,434

(22) Filed: Apr. 28, 2011

(65) Prior Publication Data

US 2011/0271746 A1 Nov. 10, 2011

(30) Foreign Application Priority Data

May 6, 2010 (JP) ................................. 2010-106802

(51) Int. Cl.
*B07C 5/00* (2006.01)
*B01L 3/00* (2006.01)

(52) U.S. Cl.
USPC ............ 209/552; 209/906; 422/502; 422/503

(58) Field of Classification Search
USPC .................. 209/3.1, 128, 129, 552, 576, 906; 422/99, 101, 104, 186.13, 502–504, 422/545; 435/4; 436/63
See application file for complete search history.

(56) References Cited

U.S. PATENT DOCUMENTS

| | | | | |
|---|---|---|---|---|
| 3,963,606 A | * | 6/1976 | Hogg | 209/3 |
| 4,279,345 A | * | 7/1981 | Allred | 209/3.2 |
| 4,338,024 A | * | 7/1982 | Bolz et al. | 356/23 |
| 5,007,732 A | * | 4/1991 | Ohki et al. | 356/73 |
| 6,432,630 B1 | * | 8/2002 | Blankenstein | 435/4 |
| 6,881,580 B2 | * | 4/2005 | Hall et al. | 436/63 |
| 7,355,696 B2 | * | 4/2008 | Mueth et al. | 356/244 |
| 7,746,466 B2 | * | 6/2010 | Godin et al. | 356/246 |
| 8,096,421 B2 | * | 1/2012 | Shinoda | 209/44.2 |
| 8,246,805 B2 | * | 8/2012 | Shinoda | 204/601 |
| 2004/0233424 A1 | * | 11/2004 | Lee et al. | 356/246 |
| 2006/0141618 A1 | * | 6/2006 | Yasuda et al. | 435/325 |
| 2008/0213821 A1 | * | 9/2008 | Liu et al. | 435/39 |

(Continued)

FOREIGN PATENT DOCUMENTS

DE 38 08 798 10/1988
DE 20 2005 008 763 10/2006

(Continued)

OTHER PUBLICATIONS

European Patent Office, Extended European Search Report, issued in connection with European Patent Application Serial No. 11003575.5, dated Nov. 18, 2011. (6 pages).

(Continued)

*Primary Examiner* — Joseph C Rodriguez
(74) *Attorney, Agent, or Firm* — K&L Gates LLP

(57) ABSTRACT

Disclosed herein is a microchip including a substrate and a sample flow path within the substrate. The sample flow path includes a changing flow path and a microtube connected to the changing flow path. The changing flow path is configured to change a cross sectional shape of the sample flow path from a quadrangular shape at a first end to a circular shape at a second end. The microtube is connected to the second end of the changing flow path and is disposed within the substrate.

50 Claims, 14 Drawing Sheets

(56) References Cited

U.S. PATENT DOCUMENTS

| | | | |
|---|---|---|---|
| 2009/0027666 A1* | 1/2009 | Godin et al. ................ 356/246 |
| 2010/0178682 A1* | 7/2010 | Nakada et al. ............ 435/173.9 |
| 2013/0008240 A1* | 1/2013 | Ito et al. ..................... 73/61.59 |
| 2013/0121877 A1* | 5/2013 | Ono ............................ 422/68.1 |

FOREIGN PATENT DOCUMENTS

| | | |
|---|---|---|
| EP | 0 360 487 | 3/1990 |
| EP | 1542007 A1 * | 6/2005 |
| JP | 2007-46947 | 2/2007 |
| JP | 2003-107099 | 4/2009 |
| WO | 81/03224 | 11/1981 |
| WO | 02/03486 | 1/2002 |
| WO | 2010/095391 | 8/2010 |

OTHER PUBLICATIONS

"Additional Volume of Cell Engineering Experimental Protocol Series Flow Cytometry Capable of being Manipulated with Freedom", Shujunsha Co. Ltd., Aug. 31, 2006.

* cited by examiner

MICROPARTICLE SORTING APPARATUS, MICROCHIP AND MICROCHIP MODULE

CROSS REFERENCES TO RELATED APPLICATIONS

The present application claims priority to Japanese Priority Patent Application JP 2010-106802 filed in the Japanese Patent Office on May 6, 2010, the entire content of which is hereby incorporated by reference.

BACKGROUND

The present invention relates to a microparticle sorting apparatus, a microchip and a microchip module. More particularly, the invention relates to a microparticle sorting apparatus for discharging a droplet containing therein a microparticle after having detected characteristics of the microparticle caused to flow through a flow path formed in a microchip, and controlling a movement direction of the droplet in accordance with the characteristics of the microparticle, thereby sorting the microparticles, a microchip and a microchip module.

Heretofore, there has been used an apparatus for introducing a dispersion liquid of microparticles to a flow path, thereby optically measuring characteristics of the microparticles thus introduced to the flow path in order to discriminate the characteristics of biologically-relevant microparticles such as a cell, a microbe, and a liposome, or microparticles such as synthetic particles, for example a latex particle, a gel particle, and an industrial particle.

In particular, with respect to the biologically-relevant microparticle, an apparatus called a flow cytometer is used in many cases. The flow cytometer, for example, is described in Non-Patent Document of "Additional Volume of Cell Engineering Experimental Protocol Series Flow Cytometry Capable of being Manipulated with Freedom," by Hiromitsu Nakauchi Shujunsha Co., Ltd. second edition published on Aug. 31, 2006. Some flow cytometers are constructed so as to only aim at measuring the characteristics of the microparticles, and others are constructed so as to be capable of sorting only the microparticles each having the desired characteristics in accordance with the measurement results. Of the latter, in particular, the apparatus aimed at sorting the cells is called "a cell sorter." At the present time, with the commercially-supplied cell sorter, the characteristics of the cells can be measured at a high speed of several thousands of cells per second to several tens of thousands of cells per second, thereby sorting the cells.

With the existing flow cytometer, the characteristics such as a size and a structure of a microparticle such as a cell or a microbead are measured in the following manner. Firstly, a sample liquid solution containing therein the microparticles each as an object of a measurement in a flow cell is caused to flow in the center of a laminar flow of a sheath liquid, thereby arranging the microparticles in line within the flow cell. Next, in an optically detecting portion, a measurement light is radiated to the microparticles arranged in line and caused to flow through the flow cell, and a scattered light or a fluorescence generated from the microparticle is detected, thereby measuring the characteristics of the microparticle. Subsequently, when the sorting for the microparticles is carried out, the sample solution is prepared as a droplet containing therein the microparticle, and the droplet is then discharged to a space in the outside of the flow cell. In this case, a movement direction of the droplet is controlled, thereby sorting the microparticles each having the desired characteristics.

Japanese Patent Application No. 2007-046947 (refer to FIG. 14) discloses an apparatus composed of a fluid system, an optical system, and a sorting system. In this case, with the fluid system, cells dyed with a fluorescence standard test solution or the like are arranged in line. With the optical system, a laser beam is radiated to the cell to detect the scattered light or the fluorescence generated from the cell. Also, with the sorting system, the movement direction of the droplet discharged to the space in the outside of the flow cell is controlled.

In those existing flow cytometers (cell sorters), the flow cell part or component composing the flow path system is made of expensive quartz. Also, each of those existing flow cytometers is composed of an orifice part or component separated from the flow cell. Thus, each of those existing flow cytometers does not have such a construction as to simply undergo disposable use for a user. For this reason, there is the possibility that even when the flow cell part or component, and the orifice part or component are sufficiently cleaned every time the measurement is carried out, cross-contamination of the samples are caused between the measurements. Such cross-contamination of the samples between the measurements, and the utilization of the expensive flow cell and orifice part or component become especially a large obstacle in such a case as to use the stem cells sorted by the cell sorter or the like in a regeneration medicine.

In recent years, a microchip in which an area and a flow path for carrying out an chemical and biological analysis are provided on a substrate made of silicon or a glass has been developed as the technique for solving the cross-contamination of the samples between the measurements, and the utilization of the expensive flow cell and orifice port or component. An analysis system using such a microchip is referred to as a Micro-Total-Analysis System (µ-TAS), a lab-on-chip, a biochip or the like.

A microparticle analysis technique for optically, electrically or magnetically analyzing the characteristics of the microparticle within the flow path or the area disposed on the microchip is known as an example of an application of the µ-TAS to the microparticle sorting technique. For example, Japanese Patent Application No. 2003-107099 discloses a microparticle sorting microchip having a flow path for guiding a liquid solution containing therein microparticles, a sheath flow forming path disposed at least on one side portion of the flow path, a microparticle measuring portion, and two or more microparticle sorting flow paths on a substrate. In this case, the microparticle measuring portion measures the microparticles introduced. Also, the two or more microparticle sorting flow paths are installed lower stream with respect to the microparticle measuring portion in order to sort and collect the microparticles. This microparticle sorting microchip has electrodes in the vicinity of a flow path hole from the microparticle measuring portion to the two or more microparticle sorting flow paths. According to a microparticle sorting apparatus including this microparticle sorting microchip, the movement direction of the microparticles can be controlled in accordance with an interaction with an electric field generated between the electrodes, thereby sorting the microparticles.

With a flow cytometer (cell sorter) to which the µ-TAS is applied, the flow path system can be composed of the microchip which can undergo the dispensable use. Therefore, no cross-contamination of the samples is generated between the measurements. In addition, since the sorting system can be constructed within an air-tight flow path disposed on the chip, the sample is prevented from being commingled with a pollutant such as an aerosol during the measurement. On the other hand, however, the liquid containing therein the microparticles needs to be fed at a high pressure to the flow path disposed on the chip, and thus the control for the movement direction of the microparticles need to be carried out in a state in which the microparticles are caused to flow within the liquid. For this reason, it is difficult to increase the flowing speed and the sorting speed of the microparticles, and thus it is difficult to measure the characteristics of the cells at the high speed of the several thousands of the cells per second to several tens of thousands of the cells per second, thereby sorting the cells like in the manner of the existing flow cytometer (cell sorter).

SUMMARY

As described above, in the existing flow cytometer (cell sorter), the flow cell composing the flow path system does not have such a construction as to be capable of undergoing disposable use. Therefore, there is the possibility that the cross-contamination of the samples between the measurements is generated. In addition, in the flow cytometer (cell sorter) to which the μ-TAS is applied, since it is difficult to increase the flowing speed and the sorting speed of the microparticles, there is caused a problem that it is difficult to realize an increased high throughput Therefore, in order to solve the problems as described above, it is desirable to provide a microparticle sorting apparatus which is capable of carrying out a high speed analysis, and safe, high-speed and inexpensive sorting by excluding cross-contamination of samples between measurements, and utilization of an expensive flow cell and an expensive orifice part or component, a microchip and a microchip module.

According to an embodiment, there is provided a microchip comprising a substrate; and a sample flow path within the substrate. The sample flow path includes: a changing flow path configured to change a cross sectional shape of the sample flow path from a quadrangular shape at a first end of the changing flow path to a circular shape at a second end of the changing flow path; and a microtube connected to the second end of the changing flow path, wherein the microtube is disposed within the substrate.

The microchip according to the embodiment may further comprise a suction flow path having a first end in communication with the sample flow path and a second end connected to a negative pressure source.

In the microchip according to the embodiment, the first end of the suction flow path may further be provided upstream of the changing flow path with respect to a sample flow direction.

In the microchip according to the embodiment, the microtube may be composed of a material selected from the group consisting of a metal, a ceramic, quartz or a resin.

In the microchip according to the embodiment, a noble metal film may be formed on a surface of the microtube.

In the microchip according to the embodiment, the inner diameter of the microtube may range from about 20 μm to about 500 μm.

In the microchip according to the embodiment, the sample flow path may include a second microtube connected to a sample liquid inlet.

In the microchip according to the embodiment, the microchip may comprise a sheath liquid inlet.

In the microchip according to the embodiment, the sample flow path may include a narrowing flow path in which a cross sectional area perpendicular to a sample flow direction becomes smaller in the sample flow direction.

In the microchip according to the embodiment, the microchip may be composed of a material selected from the group consisting of a glass and a plastic.

According to another embodiment, there is provided a microparticle sorting apparatus comprising: a microchip; a detecting section; and paired electrodes. The microchip includes: a substrate; and a sample flow path within the substrate, wherein the sample flow path includes: a changing flow path configured to change a cross sectional shape of the sample flow path from a quadrangular shape at a first end of the changing flow path to a circular shape at a second end of the changing flow path; and a microtube connected to the second end of the changing flow path, wherein the microtube is disposed within the substrate. The detecting section detects characteristics of a microparticle which is caused to flow through the sample flow path. The paired electrodes control a movement of the microparticle to a specific portion of a collection section based on the characteristics detected by the detecting section.

In the microparticle sorting apparatus according to the embodiment, the microchip may further include a suction flow path having a first end in communication with the sample flow path and a second end connected to a negative pressure source.

In the microparticle sorting apparatus according to the embodiment, the first end of the suction flow path may further be provided upstream of the changing flow path with respect to a sample flow direction.

In the microparticle sorting apparatus according to the embodiment, the microtube may be composed of a material selected from the group consisting of a metal, a ceramic, quartz or a resin.

In the microparticle sorting apparatus according to the embodiment, a noble metal film may be formed on a surface of the microtube.

In the microparticle sorting apparatus according to the embodiment, the inner diameter of the microtube may range from about 20 μm to about 500 μm.

In the microparticle sorting apparatus according to the embodiment, the sample flow path may include a second microtube connected to a sample liquid inlet.

In the microparticle sorting apparatus according to the embodiment, the microchip may comprise a sheath liquid inlet.

In the microparticle sorting apparatus according to the embodiment, the microchip may include an electrode inlet, and the paired electrodes may be inserted in the electrode inlet.

In the microparticle sorting apparatus according to the embodiment, the sample flow path may include a narrowing flow path in which a cross sectional area perpendicular to a sample flow direction becomes smaller in the sample flow direction.

In the microparticle sorting apparatus according to the embodiment, the collection section may comprise a plurality of containers.

The microparticle sorting apparatus according to the embodiment may comprise a vibration element provided on the microchip.

The microparticle sorting apparatus according to the embodiment may include grounding electrodes.

In the microparticle sorting apparatus according to the embodiment, the microchip may be composed of a material selected from the group consisting of a glass and a plastic.

In the microparticle sorting apparatus according to the embodiment, the detecting section may comprise a laser light source, a radiation system and a detection system.

In the microparticle sorting apparatus according to the embodiment, the detecting section may detect optical, electrical or magnetic characteristics of the microparticle.

In the microparticle sorting apparatus according to the embodiment, the paired electrodes may be disposed to face each other outside the microchip.

According to an embodiment, there is provided a microchip module comprising: a microchip; a vibration element provided on the microchip; and a holder configured for holding the microchip and mounting the microchip to an apparatus. The microchip includes: a substrate; and a sample flow path within the substrate, wherein the sample flow path includes: a changing flow path configured to change a cross sectional shape of the sample flow path from a quadrangular shape at a first end of the changing flow path to a circular shape at a second end of the changing flow path; and a microtube connected to the second end of the changing flow path, wherein the microtube is disposed within the substrate.

In the microchip module according to the embodiment, the microchip may further comprise a suction flow path having a first end in communication with the sample flow path and a second end connected to a negative pressure source.

In the microchip module according to the embodiment, the first end of the suction flow path may further be provided upstream of the changing flow path with respect to a sample flow direction.

In the microchip module according to the embodiment, the microtube may be composed of a material selected from the group consisting of a metal, a ceramic, quartz or a resin.

In the microchip module according to the embodiment, a noble metal film may be formed on a surface of the microtube.

In the microchip module according to the embodiment, the inner diameter of the microtube may range from about 20 μm to about 500 μm.

In the microchip module according to the embodiment, the sample flow path may include a second microtube connected to a sample liquid inlet.

In the microchip module according to the embodiment, the microchip may comprise a sheath liquid inlet.

In the microchip module according to the embodiment, the sample flow path may include a narrowing flow path in which a cross sectional area perpendicular to a sample flow direction becomes smaller in the sample flow direction.

In the microchip module according to the embodiment, the microchip may be composed of a material selected from the group consisting of a glass and a plastic.

According to another embodiment, there is provided a method of sorting microparticles. The method comprises the steps of: causing a sample liquid containing microparticles to flow through a microchip; detecting characteristics of the microparticles; and for each particle, controlling a movement of the microparticle to a specific portion of a collection section based on the detected characteristics of the microparticle. The microchip includes: a substrate; and a sample flow path within the substrate, wherein the sample flow path includes: a changing flow path configured to change a cross sectional shape of the sample flow path from a quadrangular shape at a first end of the changing flow path to a circular shape at a second end of the changing flow path; and a microtube connected to the second end of the changing flow path, wherein the microtube is disposed within the substrate.

In the method according to the embodiment, the microchip may further comprise a suction flow path having a first end in communication with the sample flow path and a second end connected to a negative pressure source.

In the method according to the embodiment, the first end of the suction flow path may further be provided upstream of the changing flow path with respect to a sample flow direction.

In the method according to the embodiment, the microtube may be composed of a material selected from the group consisting of a metal, a ceramic, quartz or a resin.

In the method according to the embodiment, a noble metal film may be formed on a surface of the microtube.

In the method according to the embodiment, the inner diameter of the microtube may range from about 20 μm to about 500 μm.

In the method according to the embodiment, the sample flow path may include a second microtube connected to a sample liquid inlet.

In the method according to the embodiment, the microchip may comprise a sheath liquid inlet.

In the method according to the embodiment, the movement of the microparticle to a specific portion of the collection section may be controlled by paired electrodes disposed to face each other outside the microchip.

In the method according to the embodiment, the sample flow path may include a narrowing flow path in which a cross sectional area perpendicular to a sample flow direction becomes smaller in the sample flow direction.

In the method according to the embodiment, the collection section may comprise a plurality of containers.

In the method according to the embodiment, the microchip may be composed of a material selected from the group consisting of a glass and a plastic.

In the method according to the embodiment, the detected characteristics of the microparticle may be selected from the group consisting of: optical characteristics, electrical characteristics and magnetic characteristics.

Additional features and advantages are described herein, and will be apparent from the following Detailed Description and the figures.

DETAILED DESCRIPTION

Figure 1A:
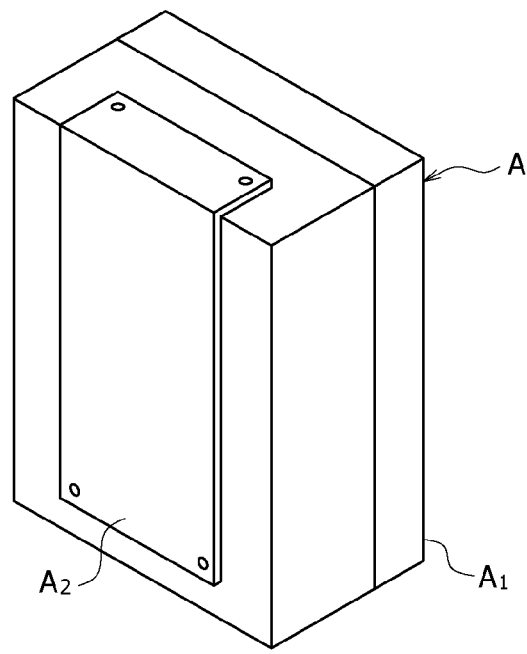
FIGS. 1A and 1B are perspective views each explaining a schematic construction of a microparticle sorting apparatus according to an embodiment.
Figure 1B:
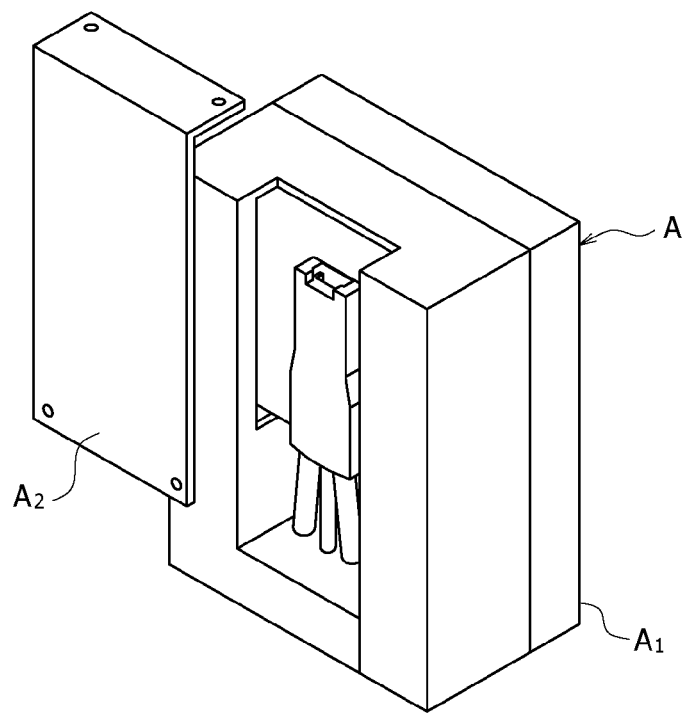
Figure 2:
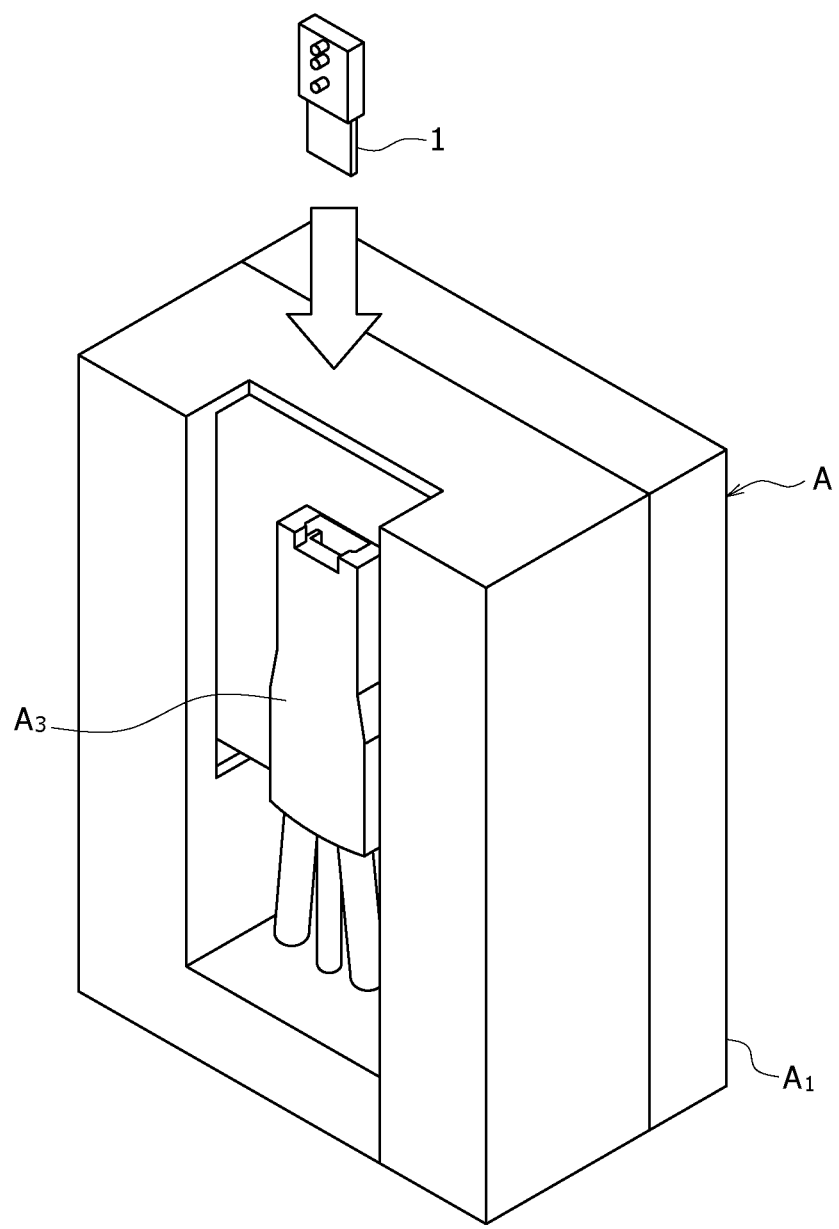
FIG. 2 is a perspective view explaining the schematic construction of the microparticle sorting apparatus according to the embodiment.
Figure 3:
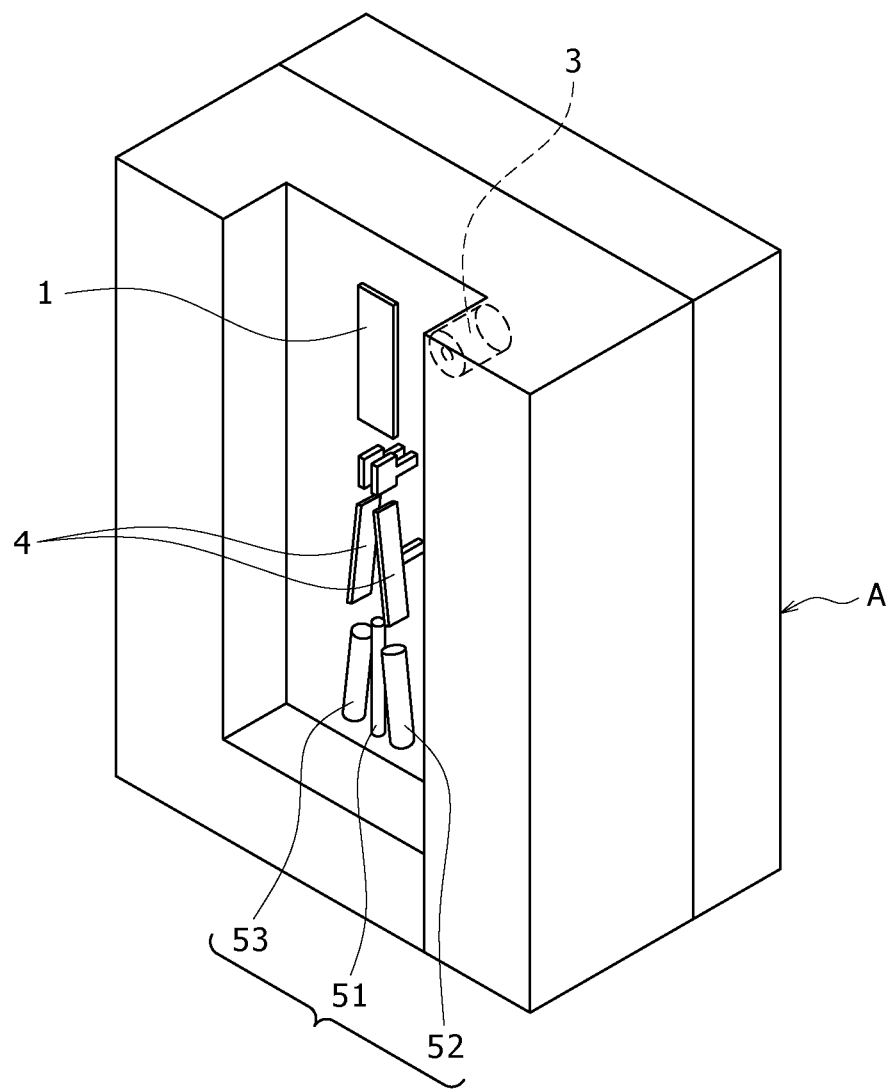
FIG. 3 is a perspective view explaining the schematic construction of the microparticle sorting apparatus according to the embodiment.

The present application will be described in detail hereinafter with reference to the accompanying drawings in accordance with an embodiment. It is noted that embodiments which will be described below are merely typical embodiments, and thus the scope of the present application is not construed in a limiting sense. The description will be made in the following order:

1. Microparticle Sorting Apparatus
2. Microchip
3. Flow Path Width and Depth in Each Portion of Microchip
4. Microchip Module
5. Operation of Microparticle Sorting Apparatus
1. Microparticle Sorting Apparatus FIGS. 1A and 1B are perspective views, respectively, each explaining a schematic construction of a microparticle sorting apparatus according to an embodiment. In FIGS. 1A and 1B, in the microparticle sorting apparatus A, a microparticle sorting field which is protected by a sorting cover $A_3$ is provided in a portion which is protected by a cover $A_2$ of a main body $A_1$. The microparticle sorting field is constructed so as to include a microchip 1 which is inserted into an upper opening of a sorting cover $A_3$ to be mounted to the sorting cover $A_3$. In FIG. 2, a block arrow indicates an insertion direction along which a microchip module having the microchip 1 as a constituent element thereof is inserted into the sorting cover $A_3$. It is noted that an illustration of the sorting cover $A_3$ is omitted in FIG. 3, and moreover, of the microchip module inserted into the sorting cover $A_3$, any of portions other than the microchip 1 is omitted in illustration.

The microparticle sorting field includes the microchip 1, an optically detecting section 3 provided in the main body $A_1$ for radiating a light to a predetermined portion of the microchip 1, and paired electrodes 4, 4 which are all provided in the main body $A_1$, and three collection sections, i.e., three containers 51, 52 and 53. The three containers 51, 52 and 53 are each detachably mounted to the main body $A_1$.

Figure 4:
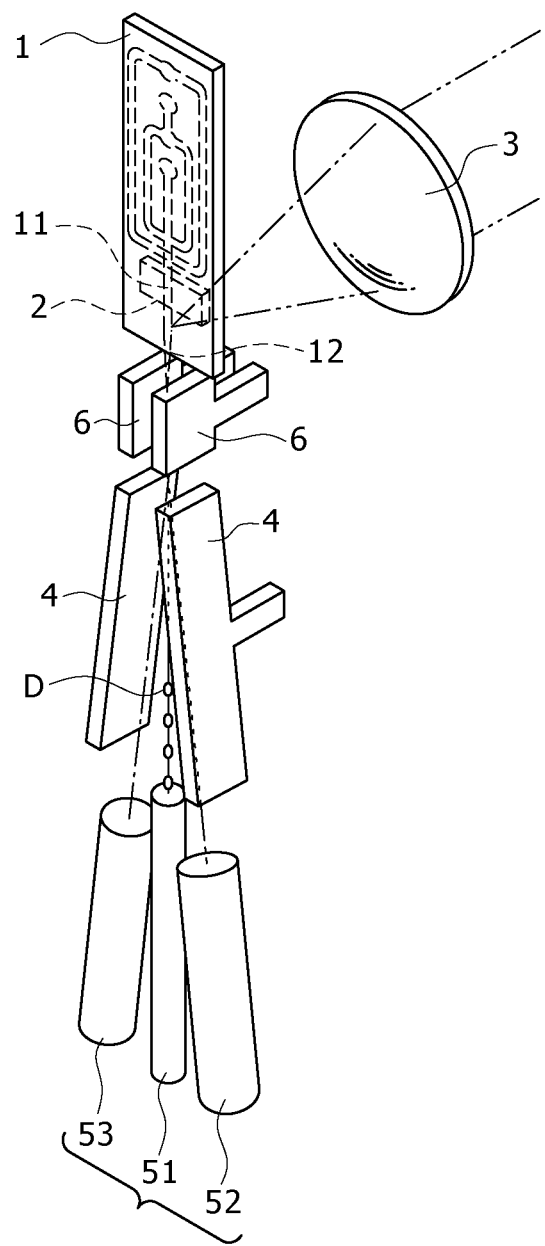
FIG. 4 is a perspective view schematically showing a skeleton construction of the schematic construction of the microparticle sorting apparatus according to the embodiment.

The construction of the microparticle sorting field will be described in detail below with reference to FIG. 4. FIG. 4 is a perspective view schematically showing a skeleton construction of the microparticle sorting apparatus A. The microchip 1, the optically detecting section 3, the paired electrodes 4, 4, and the containers 51 to 53 are shown in FIG. 4. In FIG. 4, reference symbol 2 designates a vibration element provided on the microchip 1. In addition, reference symbols 6, 6 designate grounding electrodes each grounded to the earth, respectively.

A sample flow path 11 through which a liquid (sample liquid) containing therein the microparticles each as an object of the sorting is caused to flow is formed in the microchip 1. The optically detecting section 3 radiates a light (measurement light) to a predetermined portion of the sample flow path 11, and detects a light (a light as an object of a measurement) generated from the microparticle which is caused to flow through the sample flow path 11. Hereinafter, the portion of the sample flow path 11 to which the measurement light is radiated will be referred to as "a light radiated portion" as well.

The microchip 1 can be made of a glass or any of various kinds of plastics (such as PP, PC, COP, and PDMS). The material of the microchip 1 is preferably a material which has permeability for the measurement light radiated thereto from the optically detecting section 3, is less in auto-fluorescence, and is less in optical error because wavelength dispersion is small.

Shape forming of the sample flow path 11 in the microchip 1 can be carried out by wet etching or dry etching for a substrate made of a glass, or nanoimprint, mold injection or mechanical processing for a substrate made of a plastic. The microchip 1 can be formed by encapsulating a substrate having the sample flow path 11 and the like formed thereon with a substrate made of either the same material as that of that substrate or a material different from that of that substrate.

The optically detecting section 3 can be constructed similarly to the case of the existing flow cytometer. Specifically, the optically detecting section 3 is composed of a laser light source, a radiation system, and a detection system. In this case, the radiation system is composed of a condenser lens or a dichroic mirror for condensing or radiating a laser beam to the microparticle, a band-pass filter, and the like. In addition, the detection system detects the light as the object of the measurement generated from the microparticle by the radiation of the laser beam. Also, the detection system, for example, is composed of a Photo Multiplier Tube (PMT), an area image pickup element such as a Charge Coupled Device (CCD) or a Complementary Metal-Oxide Semiconductor (CMOS), and the like. It is noted that in FIG. 4, only the condenser lens is illustrated as the optically detecting section 3. In addition, although FIG. 4 shows the case where the radiation system and the detection system are constructed by the same optical path, the radiation system and the detection system may also be constructed by different optical paths, respectively.

The light as the object of the measurement detected by the detection system of the optically detecting section 3 is a light generated from the microparticle by the radiation of the measurement light. Thus, the light as the object of the measurement, for example, may be a forward-scattered light, a laterally-scattered light, a scattered light due to Rayleigh scattering or Mie scattering, the fluorescence or the like. These lights each as the object of the measurement are converted into electrical signals, and the optical characteristics of the microparticles are detected in accordance with the resulting electrical signal.

The sample liquid which has passed through the light radiated portion is discharged from an orifice 12 provided in one end of the sample flow path 11 to a space in the outside of the microchip 1. In this case, the microchip 1 can be vibrated by the vibration element 2 to change the sample liquid into a droplet, thereby discharging the resulting droplet into the space in the outside of the microchip 1. In FIG. 4, reference symbol D designates the droplet discharged to the space in the outside of the microchip 1.

The microparticles as the object of the sorting can be contained in the droplet D. The paired electrodes 4, 4 are provided along a movement direction of the droplet D discharged to the space in the outside of the microchip 1, and are disposed so as to face each other through the droplet D being moved. A changing section (not shown) gives the electric charges to the droplet D thus discharged. Thus, the paired electrodes 4, 4 control the movement direction of the droplet D by an electrical repulsive force (or an electrical attractive force) against the electric charges given to the droplet D, and guides the droplet D to corresponding one of the containers 51 to 53. Each of the containers 51 to 53 may be a test tube container made of a plastic, as shown in FIG. 4, or the like which is normally utilized, or may be a discharging plate container or the like in which 96 wells or the like are provided on a plastic substrate.

The microparticle sorting apparatus A carries out up to the detection of the characteristics of the microparticle by the optically detecting section 3 in the microchip 1. After that, the microparticle sorting apparatus A carries out the control for the movement direction of the microparticles in the space in the outside of the microchip 1. With the microparticle sorting apparatus A, the movement direction of the droplet D containing therein the microparticles is controlled by the paired electrodes 4, 4 in accordance with the optical characteristics of the microparticle detected by the optically detecting section 3, whereby the microparticle having the desired characteristics can be collected in the corresponding one of the containers 51 to 53 to be sorted.

It should be noted that in the microparticle sorting apparatus A, the optically detecting section 3, for example, may be replaced with an electrical or magnetic detecting section. When the characteristics of the microparticles are electrically or magnetically detected, the microelectrodes are provided so as to face each other on both sides of the sample flow path 11, and a resistance value, a capacitance value, an inductance value, an impedance, a change value in electric field generated between the microelectrodes, a change in magnetization, a change in magnetic field, a change magnetizing field, or the like is measured. In this case, the sorting of the microparticles is carried out in accordance with the electrical or magnetic characteristics of the microparticles.

Figure 5:
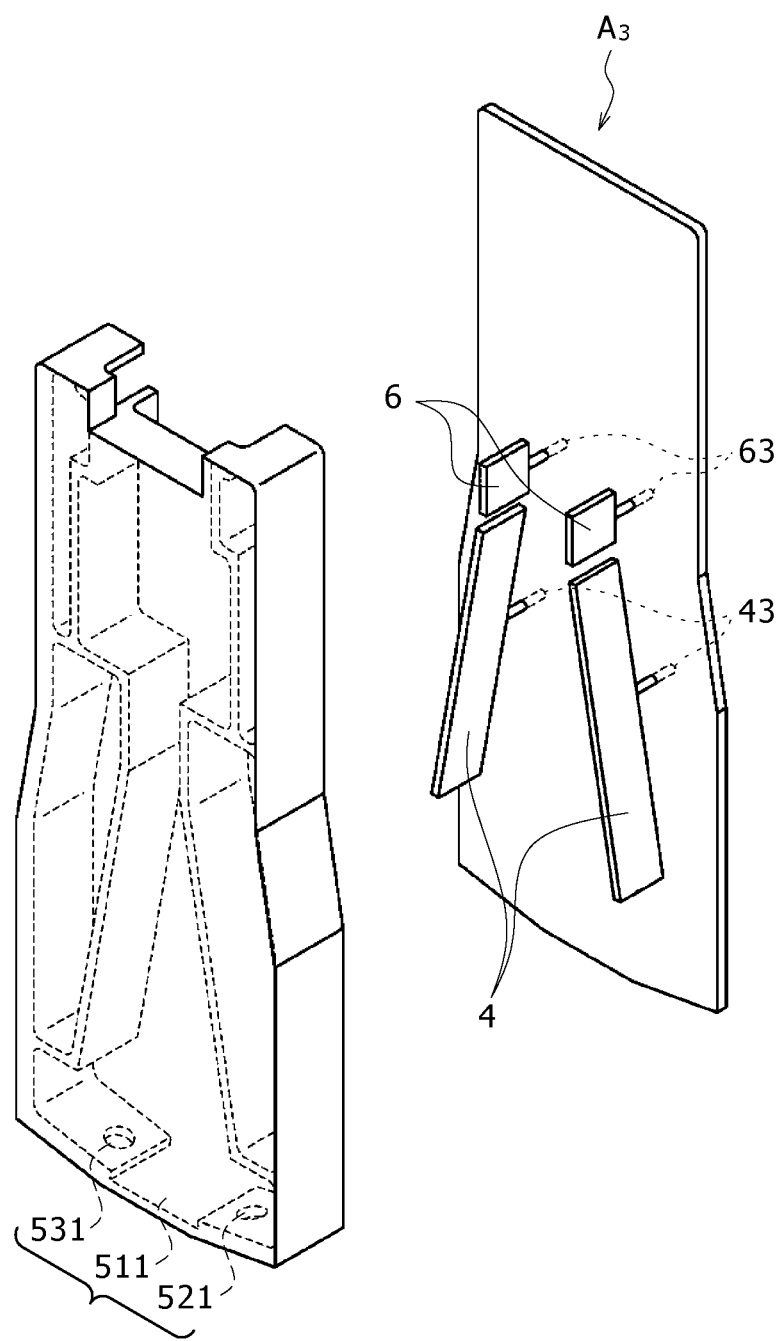
FIG. 5 is a perspective view explaining a change of the microparticle sorting apparatus according to the embodiment.

In addition, although in this case, the description has been given with respect to the case where the paired electrodes 4, 4, and the grounding electrodes 6 are fixed to the main body $A_1$ side, as shown in FIG. 5, the paired electrodes 4, 4, and the grounding electrodes 6 may also be provided on the sorting cover $A_3$ side. That is to say, the paired electrodes 4, 4 may also be provided on a cover inner side surface of a base material composing the sorting cover $A_3$ in such a way that paired electrode terminals 43, 43 through which the paired electrodes 4, 4 are electrically connected to the outside, respectively, are exposed from an outer side surface. Likewise, the grounding electrodes 6 may also be provided on the cover inner side surface of the basic material composing the sorting cover $A_3$ in such a way that grounding electrode terminals 63 through which the paired electrodes 4, 4 are electrically connected to the outside are exposed from the outer side surface. The paired electrode terminals 43, 43 and the grounding electrode terminals 63 which are exposed from the outer side surface are electrically connected to the main body $A_1$ side when they are mounted to the main body $A_1$ of the sorting cover $A_3$.

Note that, in FIG. 5, reference symbols 511, 521 and 531 designate sorting holes respectively, through which the droplet D whose movement direction is electrically controlled by the paired electrodes 4, 4 is discharged to the corresponding one of the containers 51 to 53 in the sorting cover $A_3$. For the purpose of preventing the paired electrodes 4, 4, and the grounding electrodes 6 from contacting the droplet D. preferably, as shown in FIG. 5, a partition wall for separating the movement space of the droplet D, and the paired electrodes 4, 4, or the grounding electrodes 6 from each other is provided in the base material composing the sorting cover $A_3$.

Hereinafter, details and functions of the constituent elements of the microparticle sorting apparatus A will be described in order.

2. Microchip (1) First Embodiment (1-1) Sample Flow Path

Figure 6:
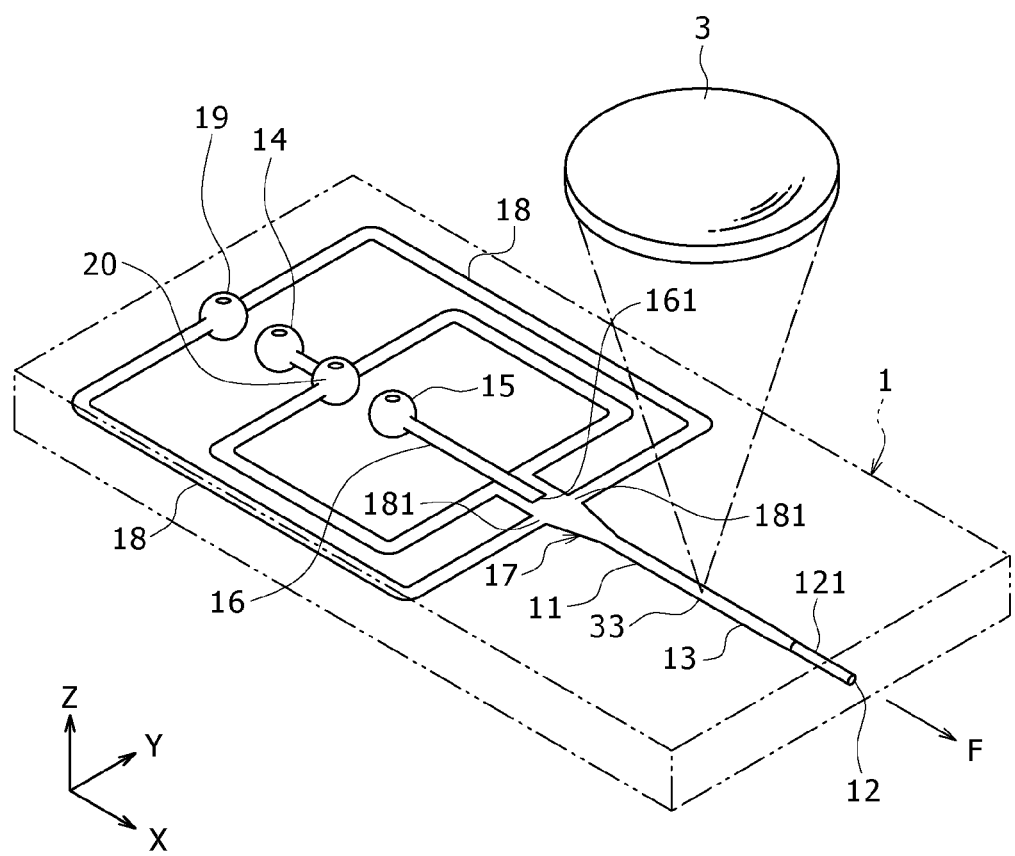
FIG. 6 is a perspective view showing a schematic construction of a microchip according to a first embodiment.

Firstly, a first embodiment of the microchip 1 will be described with reference to FIGS. 6 to 9. FIG. 6 is a perspective view showing a schematic construction of the microchip 1. A sample inlet 15, a sheath inlet 14, and a charging electrode inlet 20 are formed in the microchip 1. In this case, the sample liquid is introduced to the sample inlet 15. The sheath liquid is introduced to the sheath inlet 14. Also, the charging electrodes (charging section) dipped in the sheath liquid are inserted into the charging electrode inlet 20. After the sheath liquid introduced into the sheath inlet 14 has been caused to flow into the charging electrode inlet 20, the sheath liquid branches in two directions, i.e., in a Y-axis positive direction and in a Y-axis negative direction to be fed through the sample flow path 11. Also, after the sheath liquids are each folded twice approximately at 90°, they meet to be fed downward.

(1-2) Suction Flow Path

The suction flow path 18 having one end communicated with the sample flow path 11 is formed in the microchip 1. Reference symbol 181 designates a communication hole through which the suction flow path 18 is communicated with the sample flow path 11. A suction outlet 19 to which a suction section (negative pressure source) (not shown) is connected is formed in an end opposite to the communication hole 181 of the suction flow path 18. The suction section composed of a vacuum pump and the like gives a negative pressure to the inside of the suction flow path 18. When the sample flow path 11 (especially, a changing flow path 13 or a microtube 121 which will be described later) gets clogged with the microparticles or the bubbles, the suction section gives the negative pressure to the inside of the suction flow path 18, thereby sucking the sample liquid and the sheath liquid within the sample flow path 11 from the communication hole 181. As a result, the flow of the sample liquid and the like within the sample flow path 11 is temporarily caused to reversely flow, thereby making it possible to solve the clogging of the microparticles or the bubbles. Preferably, as shown in FIG. 6, the suction flow path 18 is provided with two flow paths as a pair. Disposition of the two suction flow paths 18 results in that even when one suction flow path 18 gets clogging with the microparticles or the bubbles which are caused to reversely flow from the sample flow path 11, the other suction flow path 18 can be operated.

(1-3) Microtube and Narrowing Flow Path

A microtube 16 for introducing the sample liquid introduced from the sample inlet 15 to the sheath liquid laminar flow is provided in a portion of the sample flow path 11 in which the two sheath liquids meet. The laminar flow of the sample liquid is caused to flow through the microtube 16 to be introduced to the sheath liquid laminar flow which is introduced from the sheath inlet 14 to be caused to flow through the sample flow path 11. As a result, the sample liquid laminar flow can be fed to the lower stream of the sample flow path 11 in a state in which the circumference thereof is surrounded by the sheath liquid laminar flow.

The communication hole 181 through which the suction flow path 18 is communicated with the sample liquid flow path 11 is preferably provided lower stream in the liquid feeding direction with respect to an opening 161 of the microtube 16. The reason for this is because when the communication hole 181 is provided upper stream with respect to the opening 161, there is the possibility that when the suction section gives the negative pressure to the inside of the suction flow path 18 to suck the sample liquid and the like within the sample flow path 11, thereby causing the sample liquid and the like to reversely flow, the microparticles or the bubbles which are being caused to reversely flow invade into the microtube 16 from the opening 161 and as a result, the microtube 16 gets clogging with the microparticles or the bubbles.

In FIG. 6, reference symbol 17 designates a narrowing flow path constructed in the sample flow path 11. The narrowing flow path 17 is formed in such a way that an area of a vertical cross section with respect to the liquid feeding direction becomes small either gradually or in a step-by-step manner from the upper stream to the lower stream in the liquid feeding direction.

Figure 7A:
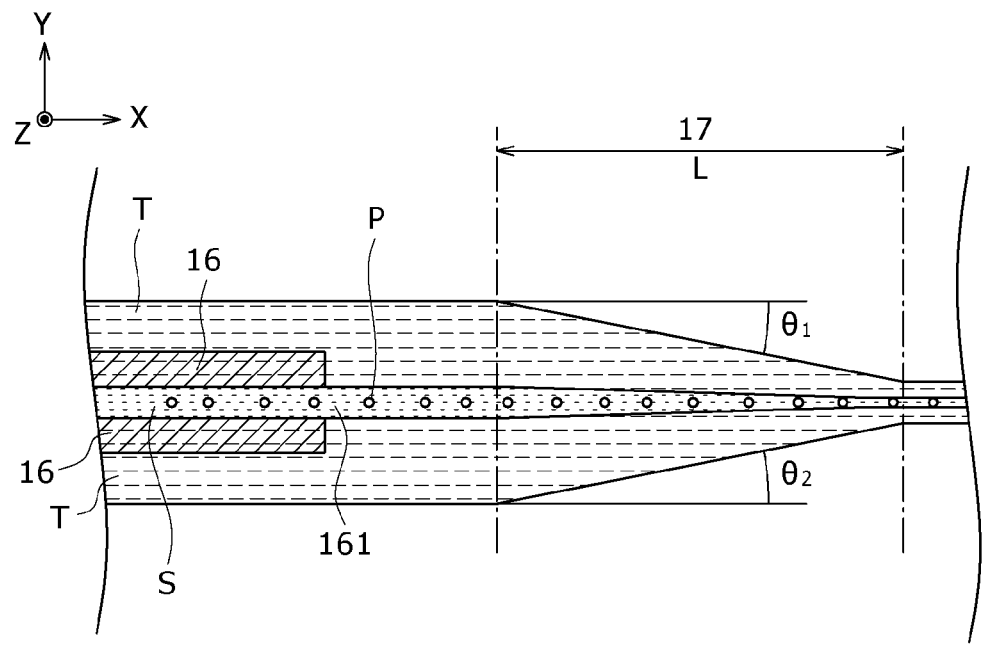
FIGS. 7A and 7B are a horizontal cross sectional view and a vertical cross sectional view, respectively, each explaining a construction of a sample flow path in the vicinity of a microtube and a narrowing flow path of the microchip, and a situation of a sample liquid laminar flow and a sheath liquid laminar flow which are caused to flow.
Figure 7B:
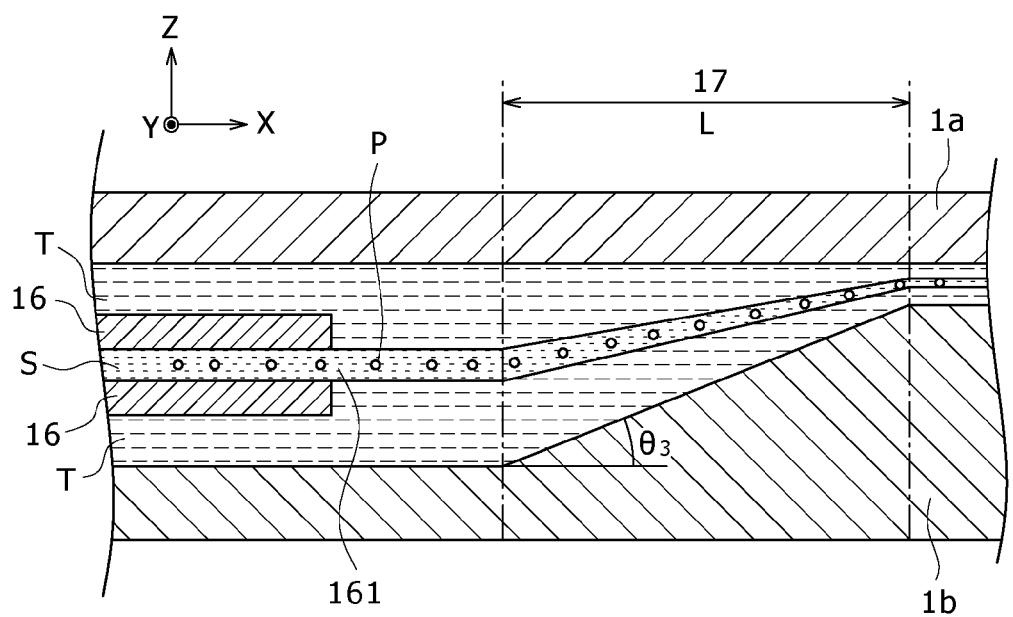

FIGS. 7A and 7B are schematic cross sectional views each explaining a construction of the sample flow path 11 in the vicinity of a portion of provision of the microtube 16, and the narrowing flow path 17, and a situation of the sample liquid laminar flow and the sheath liquid laminar flow which are caused to flow. Here, FIG. 7A shows a horizontal cross sectional view (XY cross sectional view), and FIG. 7B shows a vertical cross sectional view (ZX cross sectional view). In FIGS. 7A and 7B, reference symbol S designates the sample liquid laminar flow, reference symbol T designates the sheath liquid laminar flow, and reference symbol P designates the microparticle contained in the sample liquid. In addition, reference symbols 1a and 1b designate substrate layers, respectively. The microchip 1, the flow paths such as the sample flow path 11, and the orifice 12 are formed by sticking the substrate layers 1a and 1b to each other.

The sample liquid laminar flow S is introduced to the sheath liquid laminar flow T which is caused to flow through the sample flow path 11 by the microtube 16, and as shown in FIGS. 7A and 7B, is fed in a state (three-dimensional laminar flow) in which the sample liquid laminar flow S is surrounded by the sheath liquid laminar flow T.

A flow path sidewall of the narrowing flow path 17 is formed so as to be narrowed in the Y-axis direction in FIGS. 7A and 7B along the liquid feeding direction. Also, the narrowing flow path 17 has a weight-like shape in which the narrowing flow path 17 tapers off in terms of top surface view. By adopting the weight-like shape, the narrowing flow path 17 narrows each of widths of the laminar flows T and S of the sheath liquid and the sample liquid in the Y-axis direction to feed each of the sheath liquid laminar flow T and the sample liquid laminar flow S. In addition, the narrowing flow path 17 is formed in such a way that a flow path bottom surface thereof becomes an inclined surface in which the flow path bottom surface thereof becomes high in a depth direction (in a Z-axis positive direction) from the upper stream to the lower stream. Thus, the narrowing flow path 17 narrows each of the widths of the sheath liquid laminar flow T and the sample liquid laminar flow S in the depth direction as well.

The three-dimensional laminar flow is formed in which the sample liquid laminar flow S is surrounded by the sheath liquid laminar flow T in such a manner. The three-dimensional laminar flow is narrowed in laminar flow width thereof to be fed, whereby the microparticles P can be arranged within the sample liquid laminar flow S thus narrowed on one-by-one basis to be fed. Also, a position where the microparticle P is being fed within the sample flow path 11 is positioned, whereby the measurement light can be precisely radiated from the optically detecting section 3 to the microparticle P.

In particular, according to the narrowing flow path 17, the laminar flow width of the sample liquid laminar flow S can be narrowed not only in the horizontal direction (in the Y-axis direction in FIG. 7A) of the microchip 1, but also in the vertical direction (in the Z-axis direction in FIG. 7B) of the microchip 1. Therefore, a position of a focal point of the measurement light in the depth direction of the sample flow path 11 can be made to elaboratively agree with the position where the microparticle P is being fed. To this end, the measurement light can be precisely radiated to the microparticle P, and thus the high measurement sensitivity can be obtained.

Here, it is expected that when the sample flow path 11 is formed as a sufficient narrow flow path, and the sample liquid laminar flow S is introduced to the sheath liquid laminar flow T caused to flow through the sample flow path 11 by using the microtube 16 having a small diameter, it is also possible to form the three-dimensional laminar flow in which the laminar flow width is previously narrowed. In this case, however, reduction of the diameter of the microtube 16 results in that there is the possibility that the microtube 16 gets clogged with the microparticles P.

In the microchip 1, by providing the narrowing flow path 17, the laminar flow width can be narrowed after the three-dimensional laminar flow is formed by using the microtube 16 whose diameter is sufficiently larger than that of each of the microparticles P contained in the sample liquid. Therefore, the problem about the clogging of the microparticles 16 as described above is not caused.

FIGS. 7A and 7B show the case where the microtube 16 is provided in such a way that a center thereof is located on the same axis as that of a center of the sample flow path 11. In this case, the sample liquid laminar flow S is introduced to the center of the sheath liquid laminar flow T which is caused to flow through the sample flow path 11. The position of the sample liquid laminar flow S within the sheath liquid laminar flow T can be arbitrarily set by adjusting the opening position of the microtube 16 within the sample flow path 11. In addition, for narrowing the laminar flow width, all it takes is that the narrowing flow path 17 is formed in such a way that the area of the vertical cross section with respect to the liquid feeding direction becomes gradually small from the upper stream to the lower stream of the flow path. Thus, the shape of the narrowing flow path 17 is by no means limited to the shape shown in FIGS. 7A and 7B, and thus, for example, both the bottom surface and the upper surface of the flow path are formed as inclined surfaces, respectively, thereby making it possible to carry out the narrowing.

An inner diameter of the microtube 16 can be suitably set in accordance with the diameter of each of the microparticles P each as the object of the sorting. For example, when blood is used as the sample liquid, and the analysis of an erythrocyte or leukocyte cell is carried out, the preferable inner diameter of the microtube 16 is in the range of about 10 to about 500 µm. In addition, a width and a depth of the sample flow path 11 in the opening position of the microtube 16 may be suitably set in accordance with an outer diameter of the microtube 16 in which the diameter of each of the microparticles P is reflected. For example, when the inner diameter of the microtube 16 is in the range of about 10 to about 500 µm, preferably, each of a width and a depth of the sample flow path 11 in the opening position of the microtube 16 is in the range of about 100 to about 2,000 µm. It is noted that the cross sectional shape of the microtube 16 can also adopt an arbitrary shape such as an elliptical shape, a quadrangular shape or a triangular shape in addition to a circular shape.

The laminar flow width of each of the sample liquid laminar flow S and the sheath liquid laminar flow T before the narrowing in the narrowing flow path 17 can change depending on the width and depth of the sample flow path 11, and the diameter of the microtube 16. However, the laminar flow width of each of the sample liquid laminar flow S and the sheath liquid laminar flow T before the narrowing in the narrowing flow path 17 can be narrowed to an arbitrary laminar flow width by suitably adjusting the area of the vertical cross section with respect to the liquid feeding direction of the narrowing flow path 17. For example, in FIG. 7B, when a flow path length of the narrowing flow path 17 is taken to be L, and an inclined angle of the flow path bottom surface is taken to be $\theta_3$, a narrowed width of the three-dimensional laminar layer in the narrowing flow path 17 is expressed by (L×tan $\theta_3$). Therefore, both the flow path length L and the inclined angle $\theta_3$ are suitably adjusted, thereby making it possible to set an arbitrary narrowed width. In addition, in FIG. 7A, narrowed angles in the Y-axis direction of flow path sidewalls of the narrowing flow path 17 are taken to be $\theta_1$ and $\theta_2$, respectively, and is formed so that a relationship of "$\theta_3=2\times\theta_1$, and $\theta_1=\theta_2$" is established, whereby each of the sample liquid laminar flow S and the sheath liquid laminar flow T can be isotropically reduced, thereby narrowing the laminar flow width without disturbing the three-dimensional laminar flow formed by the microtube 16.

Here, in the first embodiment of the microchip 1, the narrowing flow path 17 does not become an essential constituent element. For example, in the case where the sample flow path 11 is formed as a sufficient narrow flow path, and the sample liquid laminar flow S is introduced to the sheath liquid laminar flow T being caused to flow through the sample flow path 11 by using the microtube 16 having the small diameter, thereby making it possible to form the three-dimensional laminar flow in which the laminar flow width is previously narrowed, the narrowing flow path 17 needs not to be provided. That is to say, the portion in which the microtube 16 is provided, and the light radiated portion which will be next described may be same in flow path width and depth to each other. In addition, such a microchip that the flow width and depth of the light radiated portion are set as being longer than the flow path width and the like of the portion in which the microtube 16 is provided is not excluded in terms of the microchip.

(1-4) Light Radiated Portion

In FIG. 6, reference symbol 33 designates the light radiated portion to which the measurement light is radiated from the optically detecting section 3. In the light radiated portion 33, the light as the object of the measurement is detected which is generated from the microparticle P by radiation of the measurement light from the optically detecting section 3.

As previously stated, the laminar flow width of each of the sample liquid laminar flow S and the sheath liquid laminar flow T is narrowed by the narrowing flow path 17. Therefore, in the light radiated portion 33, the portion of the focal point of the measurement light can be made to elaboratively agree with the liquid feeding position of the sample liquid laminar flow S within the sample flow path 11, thereby precisely radiating the measurement light to the microparticle P.

The laminar flow width of each of the sample liquid laminar flow S and the sheath liquid laminar flow T in the light radiated portion 33 can be set as an arbitrary laminar flow width by suitably adjusting the area of the vertical cross section with respect to the liquid feeding direction of the narrowing flow path 17. However, preferably, each of the width and depth of the sample flow path 11 is set in the range of about 20 to about 2,000 µm.

(1-5) Changing Flow Path and Microtube

In FIG. 6, reference symbol 12 designates an orifice for discharging the sheath liquid and the sample liquid which have passed through the light radiated portion 33 to the space in the outside of the microchip 1. The sheath liquid and the sample liquid are each changed into a droplet in the orifice 12 in accordance with an operation of a vibration element 2 which will be next described to be discharged to the outside of the microchip 1.

The orifice 12 is formed by sticking the substrate layers 1a and 1b to each other. However, when the orifice 12 is desired to be formed only by sticking the substrate layers 1a and 1b to each other, the following problems are caused. That is to say, firstly, when the orifices each having a semicircular shape are formed in the substrate layers 1a and 1b, respectively, a high precision is required for production of a die, and thus it is difficult to obtain a diameter and roundness of both the semicircular shapes within an error of several micron meters to several tens of micron meters. In addition, when the substrate layers 1a and 1b are stuck to each other, a high precision is required for alignment between both the semicircular shapes. Thus, it is difficult to produce the orifice having the high roundness. When the roundness of the orifice is low, the shapes of the droplets D discharged do not become uniform, and thus the precision of the control for the movement direction of the droplet D made by the paired electrodes 4, 4 is reduced. In addition, when the diameter of the orifice is changed, there is also encountered a problem that the die needs to be reproduced, which leads to an increase in cost.

In order to solve the problems described above, in the microchip 1, the sample flow path 11 of the orifice portion is composed of a lumen of the microtube 121 buried between the substrate layers 1a and 1b. The microtube 121 is disposed in such a way that the microtube 121 is buried in a groove formed on the same axis as that of the sample flow path 11, is sealed with an adhesive agent, and the sample liquid and the like which are fed through the sample flow path 11 is introduced to the lumen. The sample liquid and the like which are introduced to the lumen of the microtube 121 are discharged from the orifice 12 agreeing in position with an end portion of the microtube 121.

The orifice portion is composed of the microtube 121 in such a manner, whereby the orifice having the high roundness can be produced, the shape of the droplet D discharged from the orifice 12 is stabilized, and the control for the movement direction of the droplet D made by the paired electrodes 4, 4 can be carried out with high reproducibility and precision. In addition, it is only necessary to form only the groove in which the microtube 121 is intended to be buried in each of the substrate layers 1a and 1b. Therefore, an allowable error range in the alignment in the phase of the production of the die, and the sticking can be increased, and thus it becomes possible to reduce the manufacture cost of the microchip 1. Moreover, the diameter of the orifice 12 can be easily changed by suitably changing the inner diameter of the microtube 121. Thus, the reduction in cost is realized because it is unnecessary to reproduce the die as long as only the inner diameter of the microtube 121 is changed while the outer diameter of the microtube 121 is held as it is.

In the first embodiment, the description has been given with respect to the case where the sample flow path 11, the groove in which the microtube 121 is intended to be buried, and the like are formed in the substrate layer 1b, and the substrate layer 1b is stuck to the sample layer 1a. However, there may also be adopted a construction that parts of the sample flow path 11, the groove and the like are formed in the substrate layers 1a and 1b, respectively, and the substrate layers 1a and 1b are stuck to each other.

The microtube 121 can be made of a metal, ceramics, quartz, or a resin. Preferably, the microtube 121 is made either a metal or ceramics. A noble metal film made of gold, platinum or the like is preferably formed on a surface of the lumen of the microtube 121. The microtube 121 is made either a metal or ceramics, thereby making it possible to increase the durability of the orifice portion. In addition, the noble metal film is firmed on the surface of the lumen, whereby when the cell or the like is especially treated as the microparticle P, it is possible to prevent that the microparticles P are stuck to the surface of the lumen, or the lumen gets clogged with the microparticles P. A length of the flow path of the orifice portion composing the microtube 121 is set not more than 3,000 μm, preferably, not more than 100 to 500 μm, and more preferably not more than 100 to 300 μm. As a result, it is possible to suppress the loss of the liquid feeding pressure.

In FIG. 6, reference symbol 13 designates the changing flow path which is constructed in the sample flow path 11 upper stream in the liquid feeding direction with respect to the orifice 12, and lower stream with respect to the light radiated portion 33. The changing flow path 13 is a flow path for causing the cross sectional shape of the sample flow path 11 to transit to the cross sectional shape of the microtube 121. That is to say, the changing flow path 13 is constructed in such a way that the cross sectional shape of the flow path is changed from the quadrangular shape to the circular shape along the liquid feeding direction (refer to FIG. 9 as well).

In addition, the changing flow path 13 is formed in such a way that the area of the vertical cross section with respect to the liquid feeding direction becomes small either gradually or in a step-by-step manner along the liquid feeding direction. That is to say, similarly to the case of the narrowing flow path 17, the changing flow path 13 is formed in such a manner that a flow path sidewall thereof is narrowed in the Y-axis direction in FIGS. 7A and 7B along the liquid feeding direction, and a flow path bottom surface thereof becomes an inclined surface in which the flow path bottom surface thereof becomes high in the depth direction (in the Z-axis positive direction) from the upper stream to the lower stream.

Figure 8A:
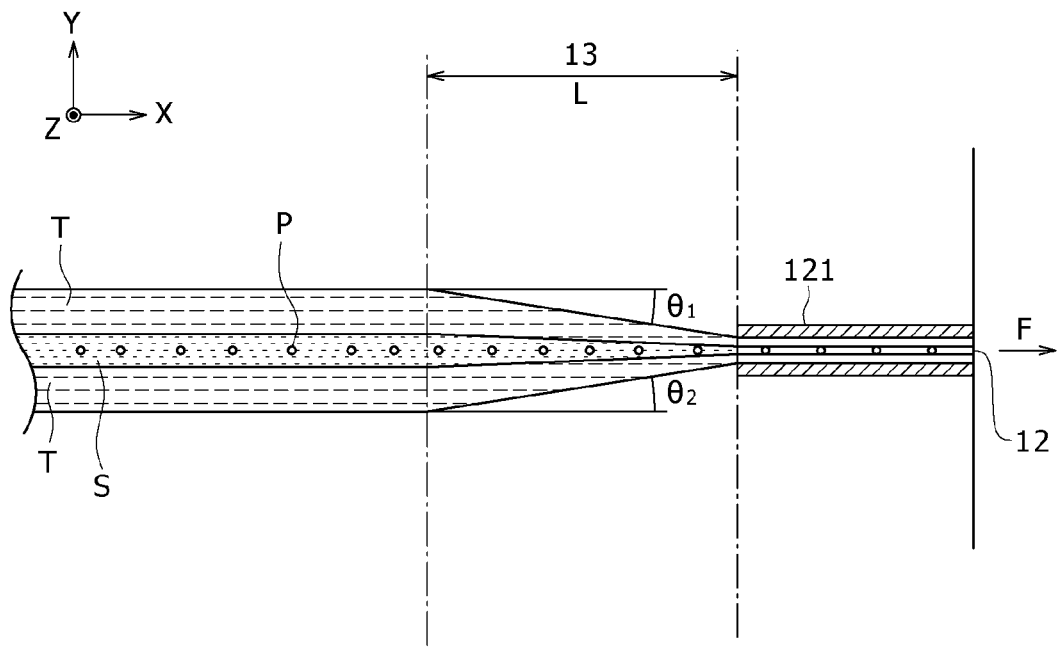
FIGS. 8A and 8B are a horizontal cross sectional view and a vertical cross sectional view, respectively, each explaining a construction of the sample flow path in the vicinity of a changing flow path and an orifice of the microchip, and a situation of the sample liquid laminar flow and the sheath liquid laminar flow which are caused to flow.
Figure 8B:
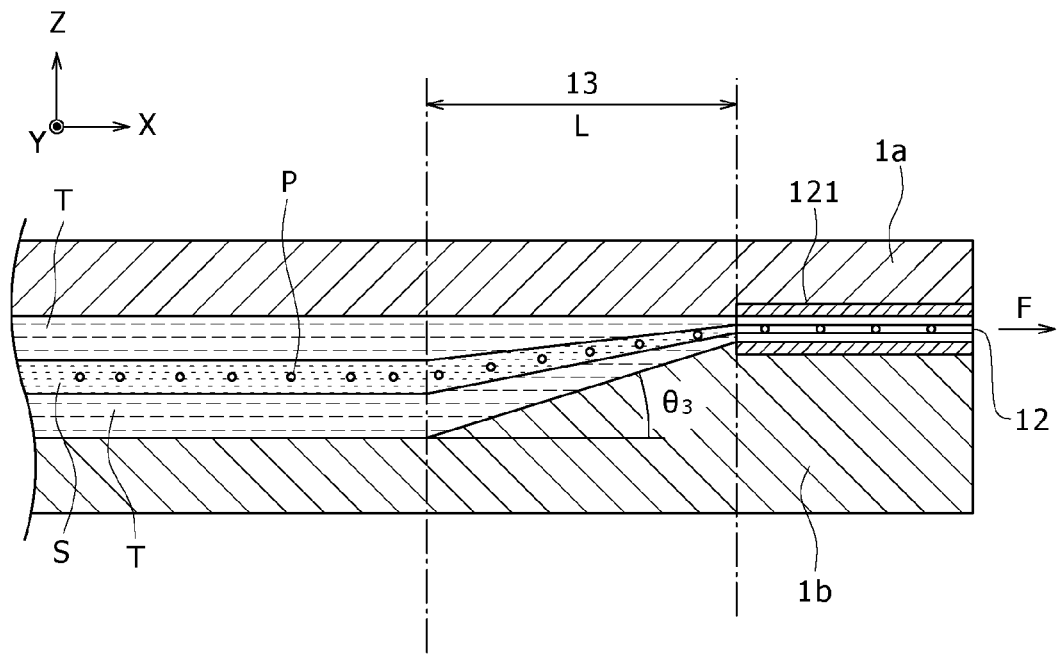
Figure 9:
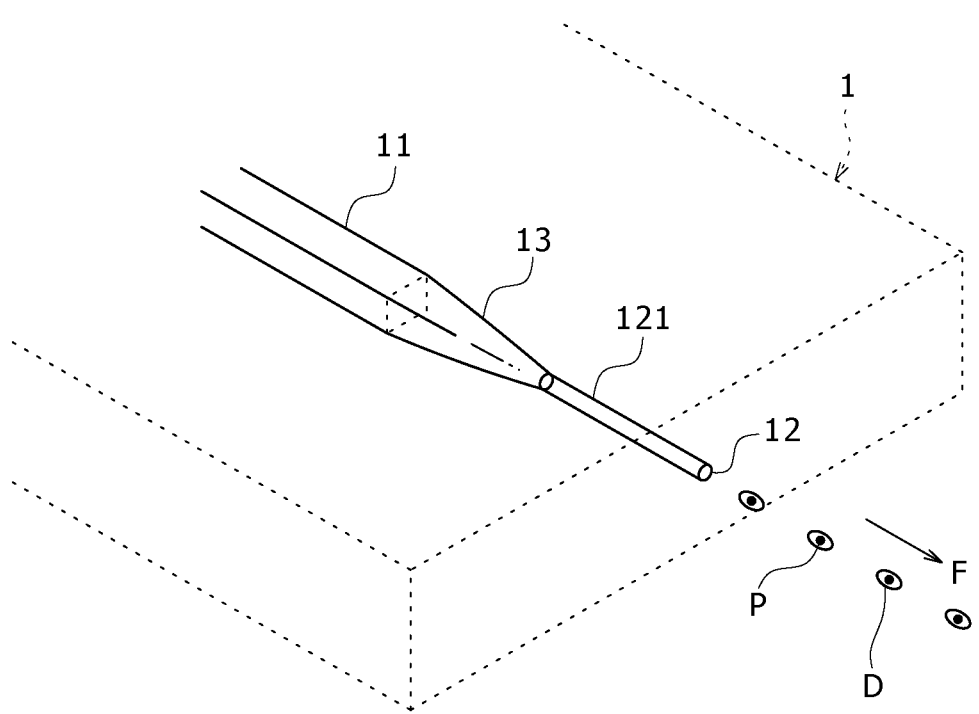
FIG. 9 is a perspective view schematically showing a construction of the sample flow path in the vicinity of the changing flow path and the orifice of the microchip, and a sample liquid and a sheath liquid which are changed into a droplet to be discharged from the orifice.

FIGS. 8A and 8B are schematic cross sectional views, respectively, each explaining a construction of the sample flow path 11 in the vicinity of the changing flow path 13 and the orifice 12, and a situation of the sample liquid laminar flow and the sheath liquid laminar flow which are caused to flow. Here, FIG. 8A is a horizontal cross sectional view (XY cross sectional view), and FIG. 8B is a vertical cross sectional view (ZX cross sectional view). In FIGS. 8A and 8B, reference symbol S designates the sample liquid laminar flow, reference symbol T designates the sheath liquid laminar flow, and reference symbol P designates the microparticle contained in the sample liquid. In addition, FIG. 9 is a perspective view schematically showing a construction of the sample flow path 11 in the vicinity of the changing flow path 13 and the orifice 12, and the sample liquid and the sheath liquid which are changed into the droplet D to be discharged from the orifice 12.

The changing flow path 13 is constructed in such a way that the cross sectional shape of the flow path is changed from the quadrangular shape to the circular shape along the liquid feeding direction. As a result, the laminar flow width of each of the sample liquid laminar flow S and the sheath liquid laminar flow T is narrowed in the Y-axis direction and in the Z-axis direction in FIGS. 8A and 8B while the three-dimensional laminar flow formed by the microtube 16 is held as it is. Thus, each of the sample liquid laminar flow S and the sheath liquid laminar flow T is introduced to the lumen of the microtube 121. Narrowing the laminar flow width results in an increase in liquid feeding pressure for the sample liquid and the sheath liquid within the sample flow path 11, and thus each of the sample liquid and the sheath liquid is discharged from the orifice 12 at a high pressure. By increasing the pressure at which each of the sample liquid and the like is discharged from the orifice 12, the droplets D can be formed at a high frequency in the orifice 12, thereby allowing the microparticles to be sorted at a high speed. In FIGS. 8A and 8B, the movement direction of the droplets D discharged is indicated by reference symbol F.

Since the laminar flow width is largely narrowed in the changing flow path 13 and in the lumen of the microtube 121, there is the possibility that each of the changing flow path 13 and the lumen of the microtube 121 gets clogged with the microparticles P or the bubbles. When each of the changing flow path 13 and the lumen of the microtube 121 gets clogged with the microparticles P, the suction section gives the negative pressure to the inside of the suction flow path 18, the flow of the sample liquid and the like within the sample flow path 11 is temporarily caused to reversely flow, thereby solving the clogging of the microparticles P or the bubbles. For this reason, the communication hole 181 through which the suction flow path 18 is communicated with the sample flow path 11 is provided upper stream in the liquid feeding direction with respect to the changing flow path 13.

The laminar flow width of each of the sample liquid laminar flow S and the sheath liquid laminar flow T before the narrowing in the narrowing flow path 17 can be narrowed to an arbitrary laminar flow width by suitably adjusting the area of the vertical cross section with respect to the liquid feeding direction of the changing flow path 13. For example, in FIG. 8B, when a flow path length of the changing flow path 13 is taken to be L, and an inclined angle of the flow path bottom surface is taken to be $\theta_3$, a narrowed width of the three-dimensional laminar layer in the changing flow path 13 is expressed by $(L \times \tan\theta_3)$. Therefore, both the flow path length L and the inclined angle $\theta_3$ are suitably adjusted, thereby making it possible to set an arbitrary narrowed width. Preferably, the laminar flow width (diameter) of each of the sample liquid laminar flow S and the sheath liquid laminar flow T in the microtube 121 is in the range about 20 to about 500 μm.

It should be noted that it is same to the case of the narrowing flow path 17 that the narrowing of the laminar flow width of each of the sample liquid laminar flow S and the sheath liquid laminar flow T can be carried out by forming both the flow path bottom surface and upper surface of the changing flow path 13 as the inclined surfaces, respectively, and the shape of the changing flow path 13 is by no means limited to the shape shown in FIGS. 8A and 8B. In addition, it is also as described with reference to the narrowing flow path 17 that when in FIG. 8A, narrowed angles in the Y-axis direction of the flow path sidewalls of the changing flow path 13 are taken to be $\theta_1$ and $\theta_2$, respectively, and a narrowed angle in the Z-axis direction is taken to be $\theta_3$, the changing flow path 13 is formed so that the relationship of "$\theta_3=2\times\theta_1$, and $\theta_1=\theta_2$" is established, whereby the three-dimensional laminar layer formed by the microtube 16 can be isotropically reduced, thereby narrowing the laminar flow without disturbing the three-dimensional laminar layer.

Here, in the first embodiment of the microchip 1, the changing flow path 13 may not be formed in such a way that the area of the vertical cross section with respect to the liquid feeding direction of the changing flow path 13 becomes small along the liquid feeding direction in some cases. For example, when the narrowing of the laminar flow width of the three-dimensional laminar flow by the narrowing flow path 17 described above is sufficiently carried out, the cross section of the changing flow path 13 may be changed only in shape thereof. In addition, for example, even when the inner diameter of the microtube 121 is sufficiently larger than each of the flow path width and depth of the light radiated portion 33, the cross section of the changing flow path 13 may be changed only in shape thereof. That is to say, in these cases, the flow path cross sectional area of the light radiated portion 33, and the flow path cross sectional area of the microtube 121 may be same to each other. Moreover, such a microchip that the cross sectional area of the changing flow path 13 is set as being larger than the flow path cross sectional of the light radiated portion 33 is not excluded in terms of the microchip of the embodiment.

(2) Second Embodiment (2-1) Changing Flow Path and Microtube

Next, a second embodiment of the microchip 101 will be described with reference to FIGS. 10A and 10B, and FIG. 11.

Constructions of the microchip 101 about the sample flow path, the suction flow path, the microtube, the narrowing flow path, and the light radiated portion are same to those of the first embodiment of the microchip 1 except for a changing flow path and a microtube. For this reason, hereinafter, a description will be given with respect to only the constructions of the changing flow path and the microtube of the microchip 101.

Figure 10A:
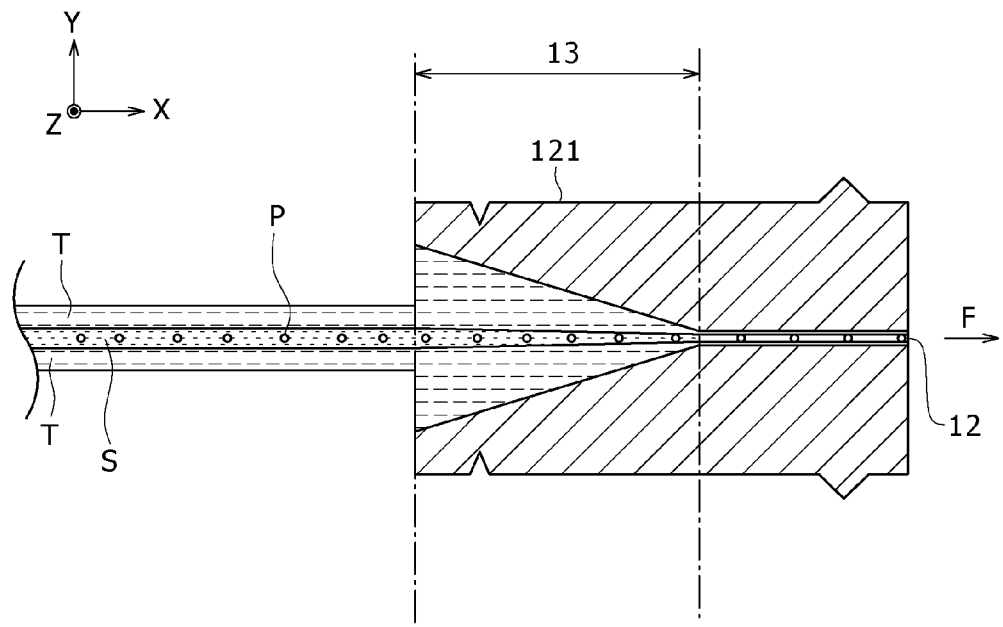
FIGS. 10A and 10B are a horizontal cross sectional view and a vertical cross sectional view, respectively, each explaining a construction of the sample flow path in the vicinity of a changing flow path and an orifice of a microchip according to a second embodiment, and a situation of the sample liquid laminar flow and the sheath liquid laminar flow which are caused to flow.
Figure 10B:
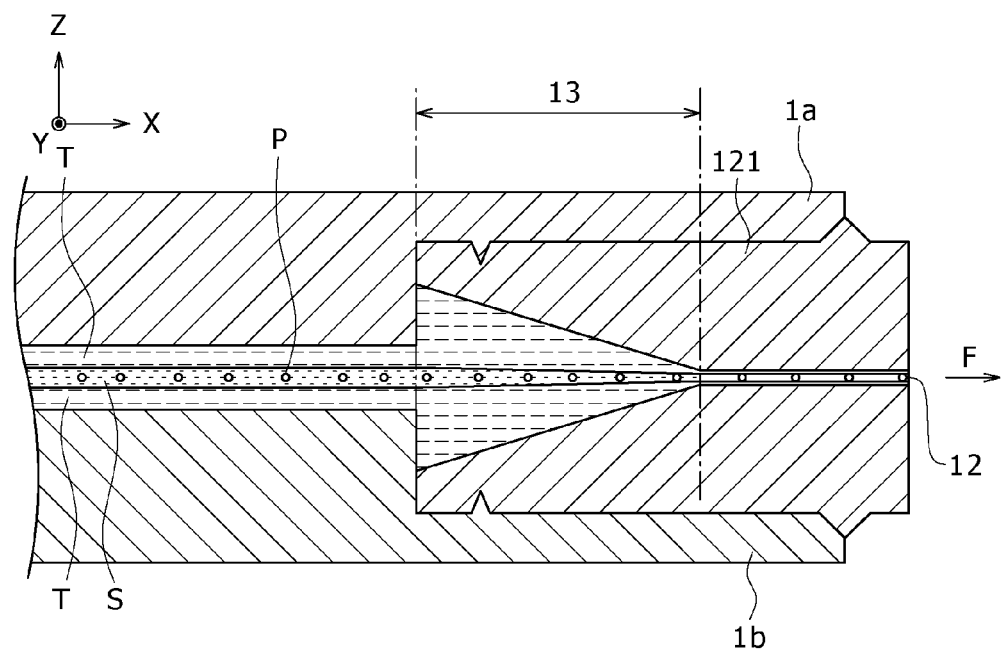
Figure 11:
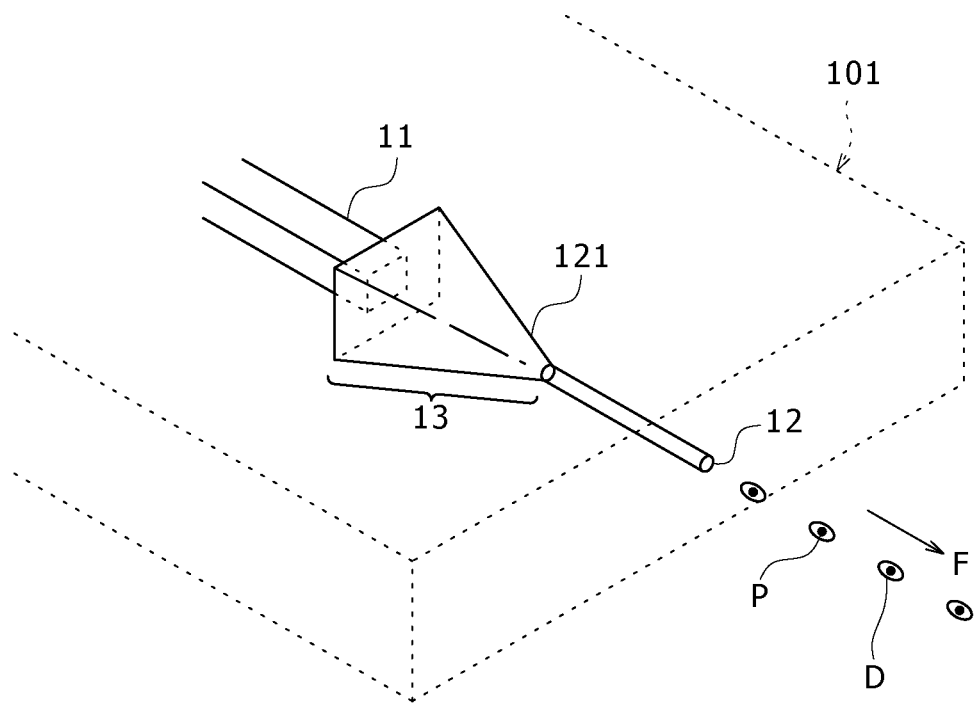
FIG. 11 is a perspective view schematically showing a construction of the sample flow path in the vicinity of the changing flow path and the orifice of the microchip, and a sample liquid and a sheath liquid which are changed into a droplet to be discharged from the orifice.

FIGS. 10A and 10B are schematic cross sectional views, respectively, each explaining a construction of the sample flow path 11 in the vicinity of the changing flow path 13 and the orifice 12, and a situation of the sample liquid laminar flow and the sheath liquid laminar flow which are caused to flow. Here, FIG. 10A is a horizontal cross sectional view (XY cross sectional view), and FIG. 10B is a vertical cross sectional view (ZX cross sectional view). In FIGS. 10A and 10B, reference symbol S designates the sample liquid laminar flow, reference symbol T designates the sheath liquid laminar flow, and reference symbol P designates the microparticle contained in the sample liquid. In addition, FIG. 11 is a perspective view schematically showing a construction of the sample flow path 11 in the vicinity of the changing flow path 13 and the orifice 12, and the sample liquid and the sheath liquid which are changed into the droplet D to be discharged from the orifice 12.

The microchip 101 is different from the microchip 1 described above in that of the sample flow path 11, in addition to the flow path of the orifice portion, the changing flow path 13 is also composed of the lumen of the microtube 121.

The microtube 121 is disposed in such a way that the microtube 121 is implanted into a hole which is formed on the same axis as that of the sample flow path 11 between the substrate layers 1a and 1b, is sealed with an adhesive agent, and thus the sample liquid and the like which are fed through the sample flow path 11 are introduced to the lumen. A snicked portion and a convex portion for increasing the adhesive property to both the substrate layers 1a and 1b is peripherally provided in an outer peripheral surface of the microtube 121.

The changing flow path 13 is formed in such a way that after the cross sectional area of the sample flow path is largely enlarged in an end surface of the microtube 121, the cross sectional area of the sample flow path becomes small along the liquid feeding direction. The flow path cross sectional area is enlarged in an inlet of the microtube 121 for the sample flow path in such a manner, whereby the laminar flow width of each of the sample liquid laminar flow S and the sheath liquid laminar flow T can be narrowed in the Y-axis direction and in the Z-axis direction in FIGS. 10A and 10B while the three-dimensional laminar flow formed by the microtube 16 is held as it is. The narrowing of the laminar flow width by the changing flow path 13 results in an increase in liquid feeding pressure for the sample liquid and the sheath liquid within the sample flow path 11, and thus each of the sample liquid and the sheath liquid is discharged from the orifice 12 at a high pressure. By increasing the pressure at which each of the sample liquid and the like is discharged from the orifice 12, the droplets D can be formed at a high frequency in the orifice 12, thereby allowing the microparticles P to be sorted at a high speed. In FIGS. 10A and 10B, the movement direction of the droplet D discharged is indicated by reference symbol F.

In FIGS. 10A and 10B, the changing flow path 13 is constructed in such a way that the cross sectional shape of the flow path is changed from the quadrangular shape to the circular shape along the liquid feeding direction. However, in the second embodiment of the microchip 101, the cross sectional shape of the changing flow path 13 may also be continuously formed as a circular shape. That is to say, when the flow path cross section in the inlet of the microtube 121 of the sample flow path 11 is enlarged so as to be sufficiently larger than that in the orifice portion, the changing flow path 13 can be formed as a conical shape.

3. Flow Path Width and Depth in Each Portion of Microchip

Figure 12:
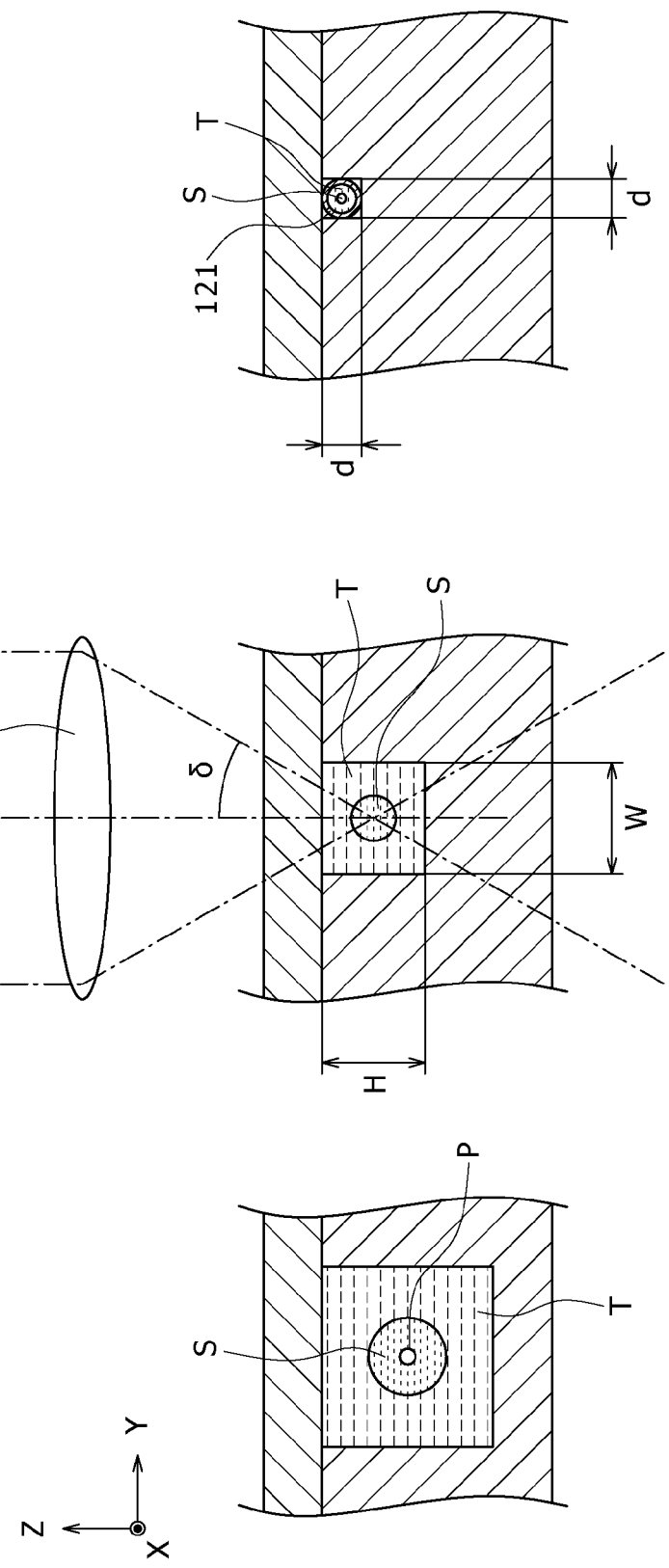
FIGS. 12A, 12B and 12C are a cross sectional view explaining a width and a depth of the sample flow path in an opening position of a microtube, a cross sectional view explaining a width and a depth of the sample flow path in a light radiated portion, and a cross sectional view explaining a width and a depth of the sample flow path in the orifice, respectively.

FIGS. 12A, 12B and 12C are schematic cross sectional views, respectively, each explaining a width and a depth of each of the portions of the sample flow path 11 in the YZ cross section. FIG. 12A shows a cross section of an opening position of the microtube 16, FIG. 12B shows a cross section of the light radiated portion 33, and FIG. 12C shows a cross section of the sample flow path 11 in the orifice 12.

As shown in FIG. 12A, in the opening position of the microtube 16, the sample liquid laminar flow S and the sheath liquid laminar flow T are fed as the three-dimensional laminar flow in which the periphery of the sample liquid laminar flow S is surrounded by the sheath liquid laminar flow T. As previously stated, each of the width and depth of the sample flow path 11 in the opening position of the microtube 16 is suitably set in accordance with the outer diameter of the microtube 16 in which the diameter of each of the microparticles P is reflected. For example, each of the width and the depth of the sample flow path 11 in the opening position of the microtube 16 is set in the range of about 100 to about 2,000 µm.

The three-dimensional laminar flow formed by the microtube 16 is fed to the light radiated portion 33 in the state in which the laminar flow width of the three-dimensional laminar flow is narrowed by the narrowing flow path 17 (refer to FIGS. 7A and 7B). The three-dimensional laminar flow is narrowed in laminar flow width thereof to be fed, whereby the microparticles P are arranged within the sample liquid laminar flow S thus narrowed on one-by-one basis to be fed to the light radiated portion 33.

The laminar flow width of each of the sample liquid laminar flow S and the sheath liquid laminar flow T in the light radiated portion 33 can be arbitrarily set by suitably adjusting the area of the vertical cross section with respect to the liquid feeding direction of the narrowing flow path 17. Each of the width W and the depth H of the sample flow path 11 in the light radiated portion 33 is preferably set in the range of about 20 to about 2,000 µm in order to make an optical detection angle (a numerical aperture of an optical system) by the optically detecting section 3 sufficiently large.

In addition, preferably, with respect to the shape of the sample flow path 11 in the light radiated portion 33, the width W is made larger than the depth H, and thus the shape of the sample flow path 11 in the light radiated portion 33 is set as a rectangular shape with respect to the radiation direction of the measurement light by the optically detecting section 3. The sample flow path 11 in the light radiated portion 33 is made to have such a wide shape, thereby making it possible to obtain the large numerical aperture of the optical system.

Each of the sample liquid laminar flow S and the sheath liquid laminar flow T which have passed through the light radiated portion 33 is narrowed in laminar flow width thereof again as shown in FIGS. 8A and 8B to be fed to the orifice 12. The laminar flow width is narrowed by the changing flow path 13, thereby making it possible to increase a pressure at which each of the sample liquid and the sheath liquid is discharged from the orifice 12.

The laminar flow width of each of the sample liquid laminar flow S and the sheath liquid laminar flow T in the orifice 12 can be arbitrarily set by suitably adjusting the area of the vertical cross section with respect to the liquid feeding direction of the changing flow path 13. In order to form the high-frequency droplets D at the high speed in the orifice 12, preferably, the laminar flow width of each of the sample liquid laminar flow S and the sheath liquid laminar flow T in the orifice 12 is made small, and thus the discharge pressure for each of the sample liquid and the sheath liquid is sufficiently increased. For this reason, an inner diameter, d, of the microtube 121 composing the flow path of the orifice portion is preferably set in the range of about 20 to about 500 µm 4. Microchip Module (1) Vibration Element FIG. 13 is a perspective view showing a construction of an embodiment of a microchip module including the microchip 1 described above as a constituent element thereof.

Figure 13:
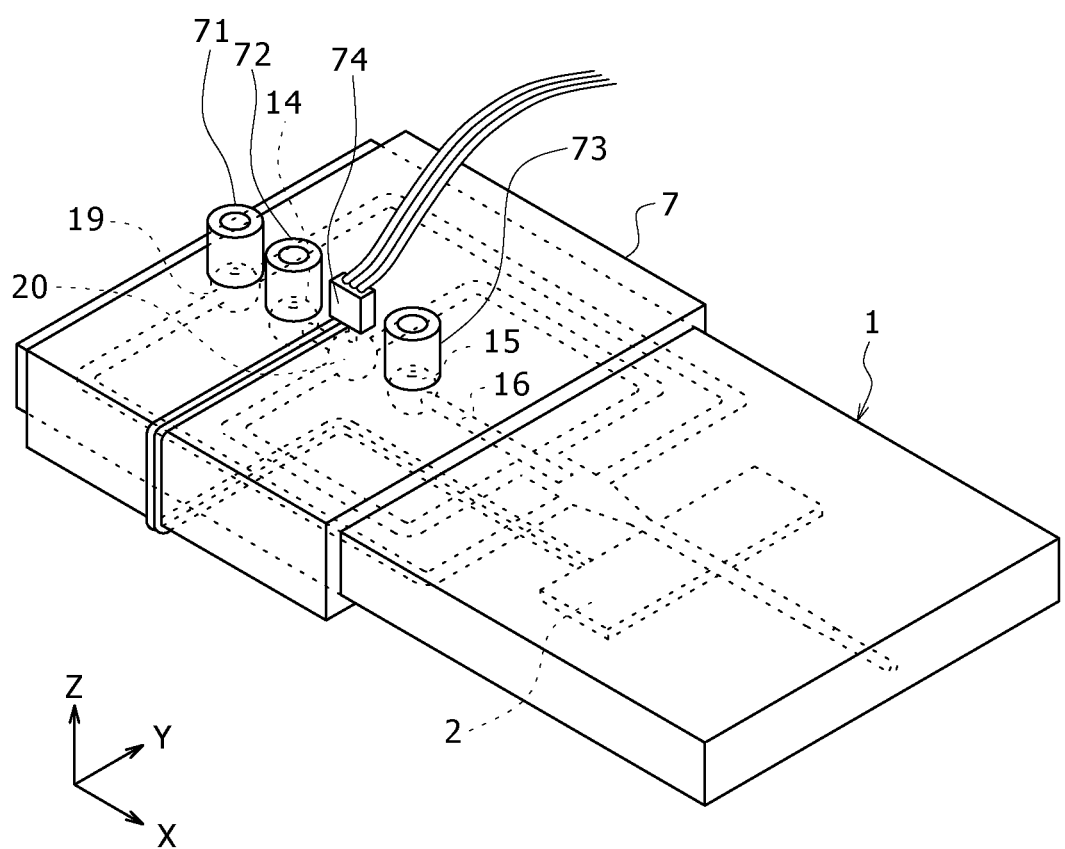
FIG. 13 is a perspective view explaining a construction of an embodiment of a microchip module according to the embodiment.

In FIG. 13, reference symbol 2 designates a vibration element provided in the microchip 1. The microchip 1 is vibrated by the vibration element 2, whereby each of the sample liquid and the sheath liquid is changed into the droplet D in the orifice 12 to be discharged to the space in the outside of the microchip 1. In addition, the vibration element 2 causes the vibration of the microchip 1 so as to have a predetermined frequency, thereby changing each of the sample liquid and the sheath liquid into the droplet D in such a way that the microparticles P are contained in the droplets D discharged on one-by-one basis (refer to FIG. 6 as well).

In this case, the vibration frequency of the vibration element 2 is set in accordance with the liquid feeding speed (flow rate) of the microparticle P detected by the optically detecting section 3 in the light radiated portion 33 (refer to FIG. 3), a resonance frequency of the microchip 1, the liquid feeding pressure in the orifice 12, the diameter of the orifice 12, and the like.

Changing each of the sample liquid and the sheath liquid into the droplet D by using such a vibration element 2 can be carried out similarly to the case of the existing flow cytometer using the flow cell. A piezo vibration element or the like which, for example, is adopted in an ink-jet printer as well is used as the vibration element 2.

The vibration element 2 is preferably disposed on a back surface of the microchip 1, that is, on a surface becoming the main body $A_1$ side in a state in which the microchip module is inserted into and mounted to the sorting cover $A_3$ (refer to FIG. 4 as well). Disposing the vibration element 2 on the back surface of the microchip 1 results in that the sample flow path is prevented from being covered by the vibration element 2 in a phase of mounting of the microchip module. For this reason, the visibility of the sample flow path is ensured, and thus it is possible to confirm whether or not the sample flow path gets clogged with the microparticles or the bubbles. In addition, for the purpose of efficiently transmitting the vibration to the orifice 12, preferably, the vibration element 2 is provided in the position close to the orifice 12. It should be noted that the vibration element 2 may also be provided on the main body $A_1$ side. In this case, the vibration element 2 may also be provided in the main body $A_1$ so as to be brought into contact with a part of the microchip 1 in the phase of the mounting of the microchip module (refer to FIG. 3).

(2) Holder and Port

In FIG. 13, reference symbol 7 designates a holder functioning as an adapter for holding the microchip 1, and mounting the microchip 1 to the main body of the microparticle sorting apparatus. Preferably, the holder 7 is made of a material having the same light permeability as that of the microchip 1 in order to ensure the visibility of the sample flow path, the suction flow path and the like which are formed in the microchip 1. As a result, when the flow path gets clogged with the microparticles or the bubbles, it is easy to confirm the position of the clogging.

In the holder 7, a suction port 71, a sheath port 72, a sample port 73, and a connector 74 are disposed on a straight line. The suction port 71 is communicated with the suction outlet 19, and a negative pressure source is connected to the suction port 71. The sheath port 72 and the sample port 73 are communicated with the sample inlet 15 and the sheath inlet 14, respectively, and the supply path of either the sample liquid or the sheath liquid is connected to each of the sheath port 72 and the sample port 73.

Two electrodes for the vibration element 2, and one charging electrode are integrated with each other in the connector 74, and wirings distributed from the main body are connected to the two electrodes for the vibration element 2, and one charging electrode, respectively. Wirings extend from the two electrodes for the vibration element 2 of the connector 74 to the vibration element 2 provided on the back surface of the microchip 1. In addition, the charging electrode of the connector 74 is inserted into the charging electrode inlet 20 of the microchip 1, and is dipped in the sheath liquid. The charging electrode functions as a charging section for giving the positive or negative charges to each of the sheath liquid and the sample liquid which are caused to flow through the sample flow path 11. Each of the sheath liquid and the sample liquid is changed into the droplet D in the orifice 12 provided in one end of the sample flow path 11 to be discharged to the space in the outside of the microchip 1. At this time, the voltage is applied to the charging electrode, thereby making it possible to give the positive or negative electric charges to the droplet D discharged.

In the embodiment of the microchip module, the suction outlet 19, the sample inlet 15, the sheath inlet 14, and the charging electrode inlet 20 are disposed in a line at the center of the microchip 1 (at the center in the Y-axis direction in FIG. 13). Also, the suction port 71, the sample port 73, the sheath port 72, and the connector 74 corresponding to the suction outlet 19, the sample inlet 15, the sheath inlet 14, and the charging electrode inlet 20, respectively, are disposed linearly on the holder 7. As a result, there is enhanced the visibility of the sample flow path, the suction flow path, and the like which are formed in the microchip 1.

5. Operation of Microparticle Sorting Apparatus

Figure 14:
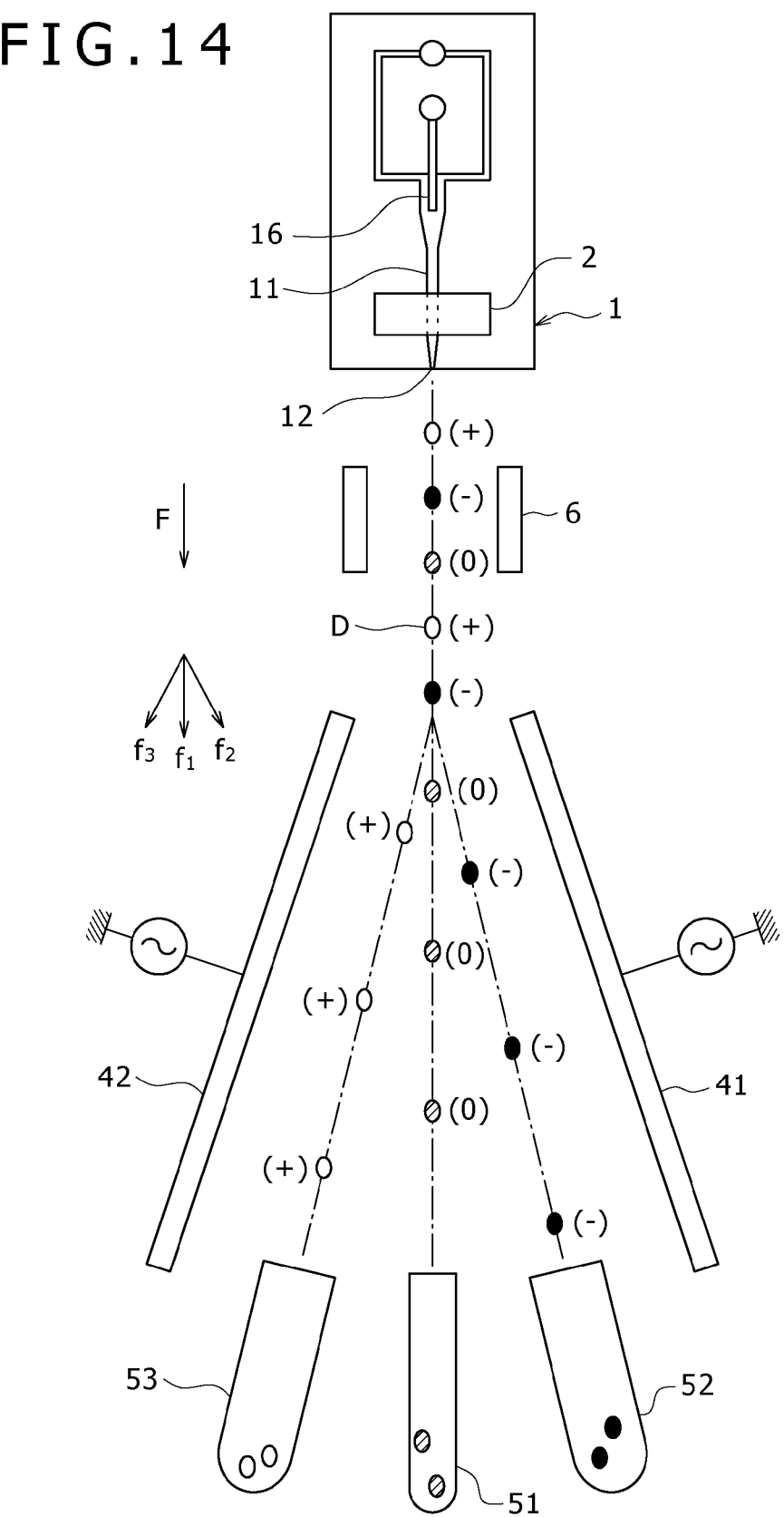
FIG. 14 is a view schematically showing sorting of the microparticles made by the microparticle sorting apparatus according to the embodiment.

Subsequently, an operation of the microparticle sorting apparatus A will be described in detail with reference to FIG. 14.

Each of the sample liquid and the sheath liquid which have passed through the light radiated portion of the sample flow path 11 is discharged from the orifice 12 to the space in the outside of the microchip 1. In the light radiated portion 33, the optically detecting section detects the liquid feeding speed (flow rate) of the microparticles P, the interval of the microparticles P, and the like concurrently with the detection of the optical characteristics of the microparticles P. The data on the optical characteristics, the flow rate, the interval and the like of the microparticles P which have been detected are converted into respective electrical signals and the resulting electrical signals are outputted to an entire control portion (not shown) of the microparticle sorting apparatus A. The entire control portion controls a vibration frequency of the vibration element 2 in accordance with those signals and vibrates the microchip 1 in such a way that the microparticles P are contained in the droplets D formed in the orifice 12 on one-by-one basis.

In addition, the entire control portion controls the voltage applied to the charging electrode inserted into the charge electrode inlet 20 so as to be syntonized within the vibration frequency of the vibration element 2. As a result, the entire control portion switches positive and negative of the electric charges given to each of the sheath liquid and the sample liquid which are caused to flow through the sample flow path 11, thereby giving the positive or negative electric charges to each of the droplets D formed in the orifice 12. The optical characteristics of the microparticle P detected by the optically detecting section are converted into the electrical signal, and the resulting electrical signal is outputted to the entire control portion. The entire control portion controls the voltage applied to the charging electrode in accordance with that electrical signal, and determines the kind of electric charge which is intended to be given to the droplet D in accordance with the optical characteristics of the microparticle P contained in each of the droplets D. Specifically, the entire control portion, for example, charges positively the droplet D containing therein the microparticle P as the object of the sorting having the desired characteristics, and charges negatively the droplet D not containing therein the microparticle P as the object of the sorting.

In this case, for the purpose of stabilizing the charging state of the droplet D, in the microparticle sorting apparatus A, the grounding electrodes 6, 6 are disposed in the vicinity of the orifice 12 along the movement direction of the droplet D discharged to the space in the outside of the microchip 1. The grounding electrodes 6, 6 are disposed so as to face each other through the droplet D being moved. Thus, the grounding electrodes 6, 6 are provided between the paired electrodes 41 and 42 for control for the movement direction of the microparticle P, and the orifice 12.

The movement direction of the charged droplet D discharged from the orifice 12 is controlled by an electric force acting between the paired electrodes 41 and 42. In this case, for precisely carrying out the control for the movement direction, it is necessary that the stable electric charges are given to the droplet D. The very high voltage is applied across the paired electrodes 41 and 42. Thus, there is the possibility that when the high potential developed across the paired electrodes 41 and 42 exerts an influence on the electric charges given to the droplet D from the microtube 16 in the orifice 12, the charging state of the droplet D becomes unstable. Then, in the microparticle sorting apparatus A, the influence by the high potential across such paired electrodes 41 and 42 is excluded by disposing the grounding electrodes 6, 6 each grounded between the orifice 12, and the paired electrodes 41 and 42.

The control for the movement direction of the droplet D discharged from the orifice 12, for example, is carried out as follows. That is to say, in the previous case where the droplet D in which the microparticle P as the object of the sorting having the desired characteristics is contained is charged positively, and the droplet D in which the microparticle P as the object of the sorting having the desired characteristics is not contained is charged negatively, one 41 of the paired electrodes 41 and 42 is charged positively, and the other 42 of the paired electrodes 41 and 42 is charged negatively, thereby making it possible to sort only the microparticle P as the object of the sorting to the container 53. Specifically, the droplet D containing therein the microparticle P as the object of the sorting having the positive electric charges given thereto is controlled in movement direction thereof in a direction indicated by an arrow $f_3$ by the electrical repulsive force against one 41 of the paired electrodes 41 and 42, and the electrical attractive force to the other 42 of the paired electrodes 41 and 42 to be introduced to the container 53. On the other hand, the droplet D not containing therein the microparticle P as the object of the sorting having the negative electric charges given thereto is controlled in movement direction thereof in a direction indicated by an arrow $f_2$ to be introduced to the container 52.

Or, for example, when no electric charge is given to the droplet D containing therein the microparticle P as the object of the sorting having the desired characteristics, the droplet D not containing therein the microparticle P as the object of the sorting is charged either positively or negatively, and the paired electrodes 41 and 42 are each charged either positively or negatively, only the microparticle P as the object of the sorting can be sorted to the container 53. Other factors such as the electric charges given to the droplet D, and the control for the movement direction of the droplet D made by the paired electrodes 41 and 42 can be carried out in various kinds of combinations similarly to the case of the existing flow cytometer. It is noted that two or more containers for collecting the respective droplets D are provided, and thus the number of containers is by no means limited to three. In addition, these containers may be constructed as exhaust paths as well for exhausting the collected droplets without pooling the collected droplets. Or, the collected microparticles P each not as the object of the sorting may also be abandoned.

Until now, the description has been given with respect to the case where the positive and negative electric charges are switched to be given to the droplet D in accordance with the characteristics of the microparticle P contained in that droplet D, thereby sorting the droplet D. However, all the droplets D are charged either with positive electric charges or with the negative electric charges, and the polarities of the voltages applied to the paired electrodes 41 and 42, respectively, are switched in accordance with the characteristics of the microparticle P, thereby making it possible to sort the droplets D. In addition, even when the optically detecting section is replaced with an electrically or magnetically detecting section, the movement direction of the droplet D is similarly controlled in accordance with the electrical or magnetic characteristics of the microparticle P, whereby the microparticle P having the desired characteristics can be collected to the corresponding one of the containers 51 to 53, thereby sorting the microparticles P.

As previously stated, in the existing flow cytometer using the flow cell, the flow cell part or component composing the flow path system for formation of the laminar flow, and the orifice part or component for formation of the droplet D are each expensive, the respective positions need to be finely adjusted (aligned with each other) so as not to disturb the laminar flow, and thus are not constructed so as to be capable of undergoing the disposable use. Therefore, there is the possibility that the cross-contamination of the samples between the measurements is generated. On the other hand, in the microparticle sorting apparatus A, the formation of the laminar flow, and the detection of the characteristics of the microparticles P are carried out in the microchip 1 in which the flow cell part or component and the orifice part or component are integrated with each other so as to be capable of undergoing the disposable use. As a result, no cross-contamination of the samples between the measurements is generated. In addition, the alignment becomes unnecessary unlike the related art, and thus a user can more easily carry out the sorting.

In addition, with the microparticle sorting apparatus A, the control for the movement direction of the microparticle P is carried out in the space in the outside of the microchip 1, whereby the control for the movement direction of the microparticle P needs not to be carried out in the liquid being caused to flow unlike the existing flow cytometer using the μ-TAS, and it is possible to attain the higher sorting speed. In addition, with the microparticle sorting apparatus A, the liquid feeding pressure for the sample liquid and the sheath liquid is sufficiently increased within the sample flow path 11, and thus the high-frequency droplets can be discharged at the high speed from the orifice 12, thereby obtaining the high sorting speed.

It should be understood that various changes and modifications to the presently preferred embodiments described herein will be apparent to those skilled in the art. Such changes and modifications can be made without departing from the spirit and scope and without diminishing its intended advantages. It is therefore intended that such changes and modifications be covered by the appended claims.

The invention claimed is:

1. A microchip comprising:
   a substrate; and
   a sample flow path within the substrate;
   wherein the sample flow path includes:
      a changing flow path configured to change a cross sectional shape of the sample flow path from a quadrangular shape at a first end of the changing flow path to a circular shape at a second end of the changing flow path; and
      a microtube connected to the second end of the changing flow path, wherein the microtube is disposed within at least one recess formed into the substrate.

2. The microchip according to claim 1, further comprising a suction flow path having a first end in communication with the sample flow path and a second end connected to a negative pressure source.

3. The microchip according to claim 2, wherein the first end of the suction flow path is provided upstream of the changing flow path with respect to a sample flow direction.

4. The microchip according to claim 1, wherein the microtube is composed of a material selected from the group consisting of a metal, a ceramic, quartz or a resin.

5. The microchip according to claim 1, wherein a noble metal film is formed on a surface of the microtube.

6. The microchip according to claim 1, wherein the inner diameter of the microtube ranges from about 20 μm to about 500 μm.

7. The microchip according to claim 1, wherein the sample flow path comprises a second microtube connected to a sample liquid inlet.

8. The microchip according to claim 1, wherein the microchip comprises a sheath liquid inlet.

9. The microchip according to claim 1, wherein the sample flow path includes a narrowing flow path in which a cross sectional area perpendicular to a sample flow direction becomes smaller in the sample flow direction.

10. The microchip according to claim 1, wherein the microchip is composed of a material selected from the group consisting of a glass and a plastic.

11. A microparticle sorting apparatus comprising:
    a microchip including:
       a substrate; and
       a sample flow path within the substrate;
       wherein the sample flow path includes:
          a changing flow path configured to change a cross sectional shape of the sample flow path from a quadrangular shape at a first end of the changing flow path to a circular shape at a second end of the changing flow path; and
          a microtube connected to the second end of the changing flow path, wherein the microtube is disposed within at least one recess formed into the substrate;
    a detecting section that detects characteristics of a microparticle which is caused to flow through the sample flow path; and
    paired electrodes which control a movement of the microparticle to a specific portion of a collection section based on the characteristics detected by the detecting section.

12. The microparticle sorting apparatus according to claim 11, wherein the microchip comprises a suction flow path having a first end in communication with the sample flow path and a second end connected to a negative pressure source.

13. The microparticle sorting apparatus according to claim 12, wherein the first end of the suction flow path is provided upstream of the changing flow path with respect to a sample flow direction.

14. The microparticle sorting apparatus according to claim 11, wherein the microtube is composed of a material selected from the group consisting of a metal, a ceramic, quartz or a resin.

15. The microparticle sorting apparatus according to claim 11, wherein a noble metal film is formed on a surface of the microtube.

16. The microparticle sorting apparatus according to claim 11, wherein the inner diameter of the microtube ranges from about 20 μm to about 500 μm.

17. The microparticle sorting apparatus according to claim 11, wherein the sample flow path comprises a second microtube connected to a sample liquid inlet.

18. The microparticle sorting apparatus according to claim 11, wherein the microchip comprises a sheath liquid inlet.

19. The microparticle sorting apparatus according to claim 11, wherein the microchip comprises an electrode inlet, and the paired electrodes are inserted in the electrode inlet.

20. The microparticle sorting apparatus according to claim 11, wherein the sample flow path includes a narrowing flow path in which a cross sectional area perpendicular to a sample flow direction becomes smaller in the sample flow direction.

21. The microparticle sorting apparatus according to claim 11, wherein the collection section comprises a plurality of containers.

22. The microparticle sorting apparatus according to claim 11, comprising a vibration element provided on the microchip.

23. The microparticle sorting apparatus according to claim 11, comprising grounding electrodes.

24. The microparticle sorting apparatus according to claim 11, wherein the microchip is composed of a material selected from the group consisting of a glass and a plastic.

25. The microparticle sorting apparatus according to claim 11, wherein the detecting section comprises a laser light source, a radiation system and a detection system.

26. The microparticle sorting apparatus according to claim 11, wherein the detecting section detects optical, electrical or magnetic characteristics of the microparticle.

27. The microparticle sorting apparatus according to claim 11, wherein the paired electrodes are disposed to face each other outside the microchip.

28. A microchip module comprising:
a microchip including:
a substrate; and
a sample flow path within the substrate;
wherein the sample flow path includes:
a changing flow path configured to change a cross sectional shape of the sample flow path from a quadrangular shape at a first end of the changing flow path to a circular shape at a second end of the changing flow path; and
a microtube connected to the second end of the changing flow path, wherein the microtube is disposed within at least one recess formed into the substrate;
a vibration element provided on the microchip; and
a holder configured for holding the microchip and mounting the microchip to an apparatus.

29. The microchip module according to claim 28, wherein the microchip comprises a suction flow path having a first end in communication with the sample flow path and a second end connected to a negative pressure source.

30. The microchip module according to claim 29, wherein the first end of the suction flow path is provided upstream of the changing flow path with respect to a sample flow direction.

31. The microchip module according to claim 28, wherein the microtube is composed of a material selected from the group consisting of a metal, a ceramic, quartz or a resin.

32. The microchip module according to claim 28, wherein a noble metal film is formed on a surface of the microtube.

33. The microchip module according to claim 28, wherein the inner diameter of the microtube ranges from about 20 μm to about 500 μm.

34. The microchip module according to claim 28, wherein the sample flow path comprises a second microtube connected to a sample liquid inlet.

35. The microchip module according to claim 28, wherein the microchip comprises a sheath liquid inlet.

36. The microchip module according to claim 28, wherein the sample flow path includes a narrowing flow path in which a cross sectional area perpendicular to a sample flow direction becomes smaller in the sample flow direction.

37. The microchip module according to claim 28, wherein the microchip is composed of a material selected from the group consisting of a glass and a plastic.

38. A method of sorting microparticles comprising:
causing a sample liquid containing microparticles to flow through a microchip, the microchip including:
a substrate; and
a sample flow path within the substrate;
wherein the sample flow path includes:
a changing flow path configured to change a cross sectional shape of the sample flow path from a quadrangular shape at a first end of the changing flow path to a circular shape at a second end of the changing flow path; and
a microtube connected to the second end of the changing flow path, wherein the microtube is disposed within at least one recess formed into the substrate;
detecting characteristics of the microparticles; and
for each particle, controlling a movement of the microparticle to a specific portion of a collection section based on the detected characteristics of the microparticle.

39. The method according to claim 38, wherein the microchip comprises a suction flow path having a first end in communication with the sample flow path and a second end connected to a negative pressure source.

40. The method according to claim 39, wherein the first end of the suction flow path is provided upstream of the changing flow path with respect to a sample flow direction.

41. The method according to claim 38, wherein the microtube is composed of a material selected from the group consisting of a metal, a ceramic, quartz or a resin.

42. The method according to claim 38, wherein a noble metal film is formed on a surface of the microtube.

43. The method according to claim 38, wherein the inner diameter of the microtube ranges from about 20 μm to about 500 μm.

44. The method according to claim 38, wherein the sample flow path comprises a second microtube connected to a sample liquid inlet.

45. The method according to claim 38, wherein the microchip comprises a sheath liquid inlet.

46. The method according to claim 38, wherein the movement of the microparticle to a specific portion of the collection section is controlled by paired electrodes disposed to face each other outside the microchip.

47. The method according to claim 38, wherein the sample flow path includes a narrowing flow path in which a cross sectional area perpendicular to a sample flow direction becomes smaller in the sample flow direction.

48. The method according to claim 38, wherein the collection section comprises a plurality of containers.

49. The method according to claim 38, wherein the microchip is composed of a material selected from the group consisting of a glass and a plastic.

50. The method according to claim 38, wherein the detected characteristics of the microparticle are selected from the group consisting of: optical characteristics, electrical characteristics and magnetic characteristics.

* * * * *